United States Patent
Ota et al.

(10) Patent No.: US 7,209,162 B2
(45) Date of Patent: Apr. 24, 2007

(54) ELECTRONIC ENDOSCOPE APPARATUS

(75) Inventors: Noriko Ota, Saitama (JP); Shunichi Ito, Tokyo (JP); Kenichi Iriyama, Tokyo (JP)

(73) Assignee: PENTAX Corporation, Tokyo (JP)

( * ) Notice: Subject to any disclaimer, the term of this patent is extended or adjusted under 35 U.S.C. 154(b) by 797 days.

(21) Appl. No.: 10/414,023

(22) Filed: Apr. 16, 2003

(65) Prior Publication Data

US 2003/0202090 A1   Oct. 30, 2003

(30) Foreign Application Priority Data

| Apr. 17, 2002 | (JP) | ............................ P2002-114323 |
| Apr. 17, 2002 | (JP) | ............................ P2002-114505 |
| Apr. 17, 2002 | (JP) | ............................ P2002-114833 |
| Sep. 12, 2002 | (JP) | ............................ P2002-266688 |

(51) Int. Cl.
*H04N 7/18* (2006.01)
*A61B 1/00* (2006.01)

(52) U.S. Cl. ........................................ 348/68; 600/101

(58) Field of Classification Search .................. 348/68, 348/65, 69, 77, 74, 45; 600/101, 104
See application file for complete search history.

(56) References Cited

U.S. PATENT DOCUMENTS

| 6,080,104 | A |   | 6/2000 | Ozawa et al. |   |
| 6,413,207 | B1 |   | 7/2002 | Minami |   |
| 6,677,983 | B1 | * | 1/2004 | Takahashi et al. | ............ 348/65 |
| 6,707,485 | B1 | * | 3/2004 | Higuchi et al. | ............... 348/69 |

FOREIGN PATENT DOCUMENTS

| JP | 2-193633 | 7/1990 |
| JP | 4-144389 | 5/1992 |
| JP | 6296580 | 10/1994 |
| JP | 11-244229 | 9/1999 |
| JP | 11244229 | 9/1999 |
| JP | 2000-184261 | 6/2000 |
| JP | 2001100111 | 4/2001 |

OTHER PUBLICATIONS

English Language Translation of JP Appln. No. 6-296580.
English Language Translation of JP Appln. No. 11-244229.

* cited by examiner

*Primary Examiner*—Gims Philippe
(74) *Attorney, Agent, or Firm*—Greenblum & Bernstein, P.L.C.

(57) ABSTRACT

An electronic endoscope apparatus has a moving-image displayer that reads image-pixel signals from an image sensor at predetermined time intervals to display a moving-image, a light-amount adjuster that adjusts an amount of light for illuminating a subject, and a still-image recorder that performs a series of actions for recording a still image. The still-image recorder is capable of reading the image-pixel signals at a still-image electronic shutter speed, which corresponds to a reading time interval shorter than the predetermined time interval. When the series of actions is started, the still-image recorder controls the light-amount adjuster such that the light-amount becomes a standard light-amount corresponding to the recording of the still image. Then, the still-image recorder performs a recording process in accordance with the still-image electronic shutter speed when the light-amount becomes the standard light-amount.

25 Claims, 23 Drawing Sheets

ELECTRONIC ENDOSCOPE APPARATUS

BACKGROUND OF THE INVENTION

1. Field of the Invention

The present invention relates to an electronic endoscope apparatus having a video-scope with an image sensor, especially, it relates to the recording of a still-image.

2. Description of the Related Art

In an electronic endoscope apparatus having a video-scope with an image sensor, a subject image, such as a diseased portion, is displayed on a monitor in real-time. Namely, a moving-image is displayed. Further, the electronic endoscope apparatus is capable of displaying a still-image on a monitor and recoding the still-image in an image memory. When an operator pushes a freezing switch button provided on an operating portion of the video-scope, a series of actions (so called "freeze action") is performed. Consequently, the still-image is displayed, and can be recorded, or printed.

When displaying or recording the observed portion in an organ as a still-image, the degradation of resolution or the degradation of color sharpness occurs due to a hand tremble of the video-scope, or movement of the observed portion. Consequently, the image-quality degrades. Especially, the image-quality significantly degrades when the distance between the observed portion and the distal end of the video-scope is far, or when enlarging the displayed subject image by a zooming function. To solve the above problems, it is known that, when displaying/recording the still-image, the amount of light for illuminating the subject should be increased and the electronic shutter speed of the image sensor should be set to a higher speed. In this case, the light-amount is increased by fully opening a diaphragm or by emitting a strobe light, and the electronic shutter speed is set in accordance with the increase of light-amount.

However, since the increased light-amount is predetermined regardless of quality of the still-image, the proper electronic shutter speed should be set while repeatedly recoding the still image and repeatedly judging whether the brightness of the recorded still-image is proper. Further, when the opening-degree of the diaphragm immediately before the freeze action is very small, the light-amount rapidly increases due to fully opening the diaphragm, almost instantaneously, so that a still-image with a proper brightness cannot be obtained.

SUMMARY OF THE INVENTION

Therefore, an object of the present invention is to provide an electronic endoscope apparatus capable of obtaining a still-image with proper brightness without repeatedly performing the freeze action.

An electronic endoscope apparatus including a video-scope with an image sensor according to the present invention has a moving-image displayer, a light-amount adjuster, and a still-image recorder. The moving-image displayer reads image-pixel signals from the image sensor at a predetermined time interval and processes the image-pixel signals, to display a moving-image. For example, when the NTSC standard is applied as the TV standard, the image-pixel signals are read from the image sensor at 1/60 of a second time interval. On the other hand, in the case of the PAL standard, the reading time interval is set to 1/50 second. The light-amount adjuster adjusts an amount of light for illuminating a subject. For example, a diaphragm is applied as the light-amount adjuster, whereas a liquid crystal shutter or polarizing plate may be applied. Further, an emitting-light control process may be performed for adjusting the light-amount by directly controlling the light emitted from the light source.

The still-image recorder performs a series of actions for recording a still image as data. For example, a starting member for starting the series of actions is provided on the video-scope, and the series of actions is started when the starting member is operated. The still-image recorder is capable of performing a high-speed electronic shutter action that reads the image-pixel signals at a high still-image electronic shutter speed. The still-image electronic shutter speed corresponds to an exposed time for recording the still-image as data, and is set to a higher speed compared to a normal electronic shutter speed for displaying the moving-image. Namely, the reading time interval for recording the still-image is shorter than the predetermined time interval for displaying the moving-image. The still-image electronic shutter speed is determined in accordance with the reading time interval for the moving-image, which correspond to the TV standard, the distance between the observed subject and the end portion of the video-scope, the construction of the light-amount adjuster, and so on. Especially, in the case of the diaphragm, the still-image electronic shutter speed is set on the basis of the relationship between the opening-degree of the diaphragm and the change in the light-amount.

When the series of actions is started, the still-image recorder controls the light-amount adjuster such that the light-amount becomes a standard light-amount for recording the still image. The still-image is not recorded until the light-amount becomes a standard light-amount for recording the still image. The standard light-amount indicates a light-amount necessary for obtaining a still-image with proper brightness, and is determined in accordance with the normal electronic shutter speed and the still-image electronic shutter speed. For example, when an automatic light-amount adjusting processor is provided in the electronic endoscope apparatus, to maintain constant brightness of the moving-image, the automatic light-amount adjusting processor controls the light-amount adjuster on the basis of a moving-image standard light-amount, which corresponds to the standard brightness of the moving-image. Accordingly, when adjusting the brightness of the still-image to a brightness that is the same as the brightness of the moving-image, the standard light-amount is predetermined in accordance with a ratio of the reading time intervals for the still-image to the reading time intervals for the moving-image. When the light-amount becomes the standard light-amount, the still-image recorder performs a recording process that records (stores) the still-image in a memory as data. Thus, the still-image can be displayed on a monitor, or recorded in peripheral equipment, such as a video recorder. The recording process may be performed at the same time that the light-amount becomes the standard light-amount, or may be performed after a given time has passed. For example, the still-image recorder prohibits performing the high-speed electronic shutter action and the recording process until the light-amount becomes the standard light-amount. On the other hand, the still-image recorder may perform the high-speed electronic shutter action while prohibiting the recording process, until the light-amount becomes the standard light-amount.

Since the recording process is not performed until the light-amount has become the standard light-amount, an unblured and sharp still-image with proper brightness is obtained by only one recording action.

To determine whether the light-amount is at the standard light-amount by using a simple construction, the determination of the light-amount is performed by feedback control. Namely, the still-image recorder has a light-amount determiner that determines whether the light-amount becomes the standard light-amount. The still-image recorder prohibits the recording process until it is determined that the light-amount has become the standard light-amount.

To adjust the light-amount rapidly and accurately, the still-image recorder controls the light-amount adjuster so as to gradually increase the light-amount, or increase the light-amount step by step. Consequently, the light-amount does not pass the standard light-amount while increasing to the standard light-amount. In the case of the diaphragm, the still-image recorder opens the diaphragm gradually until the light-amount becomes the standard light-amount. For example, the electronic endoscope apparatus has a luminance calculator that calculates a luminance value indicating the brightness of the subject image, on the basis of the image-pixel signals. In this case, the light-amount determiner determines whether the luminance value has become a still-image standard luminance value corresponding to the standard light-amount.

While controlling the light-amount adjuster by starting the series of actions, the light-amount for the subject increases. Consequently, the brightness of the displayed subject image abruptly changes. Accordingly, to prevent the operator from an operation mistake due to the abrupt brightness change, preferably, the electronic endoscope apparatus has a provisional still-image displayer that displays a provisional still-image when the series of actions is started. The provisional still-image displayer continually displays the provisional still image until the light-amount becomes the standard light-amount. The provisional still-image with a constant brightness is displayed, which does not create an uncomfortable feeling for the operator.

On the other hand, when performing the feed-forward control for adjusting the light-amount in place of the feedback control, the still-image recorder, in which a given control-amount necessary for achieving the standard light-amount has been previously set, controls the light-amount adjuster by the control-amount. For example, the light-amount adjuster is constructed such that the light-amount adjuster increases and decreases the light-amount in accordance with a light-amount adjusting parameter. For example, in the case of a pivotable diaphragm, the rotating angle corresponds to the light-amount adjusting parameter. In the case of a liquid crystal shutter, the impressed voltage corresponds to the light-amount adjusting parameter. On the other hand, when controlling the light emitted from the light source, the current corresponds to the light-amount adjusting parameter. The still-image recorder previously sets a given change-amount for the light-amount adjusting parameter, which is necessary for achieving the standard light-amount. Then, when the series of actions is started, the still-image controller controls the light-amount adjuster in accordance with the determined change-amount. In the case of the pivotable diaphragm, the still-image recorder previously sets a change angle-amount necessary for achieving the standard light-amount, and pivots the diaphragm by the change angle-amount. In the case of the liquid crystal shutter, the still-image recorder previously sets change voltage-amount necessary for achieving the standard light-amount, and drives the liquid crystal shutter by the change voltage-amount. To rapidly adjust the light-amount regardless of the situation of the light-amount adjuster or the degree of the light-amount for the subject, the light-amount adjuster is constructed such that the light-amount changes by a constant change-amount as the light-amount adjusting parameter changes by a constant change-amount.

On the other hand, an independent light-amount adjuster for recording the still-image as data may be provided. Namely, the light-amount adjuster has a moving-image light-amount adjuster, and a still-image light-amount adjuster. The moving-image light-amount adjuster adjusts the light-amount to adjust the brightness of the moving-image. The still-image light-amount adjuster changes the light-amount to the standard light-amount when performing the series of actions. The still-image recorder controls the still-image light-amount adjuster such that the light-amount becomes the standard light-amount. For example, the still-image light-amount adjuster is arranged in a light-pass of the light emitted from a light source, and has a transmitting member that is capable of adjusting a transmitting-amount of light emitted from the light source. For example, the transmitting member is a liquid crystal shutter. When a diaphragm is applied as the moving-image light-amount adjuster, the still-image light-amount adjuster is arranged between the light source and the diaphragm.

An apparatus for recording (storing) a still-image according to an electronic endoscope apparatus including a video-scope with an image sensor, has a high-speed electronic shutter processor that reads image-pixel signals from the image sensor at a still-image electronic shutter speed, which corresponds to a reading time interval shorter than a predetermined time interval defined for displaying a moving-image; a still-image light-amount controller that controls a light-amount adjuster for adjusting an amount of light for illuminating a subject, such that the light-amount becomes a standard light-amount corresponding to a recording of the still image, when a series of actions for recording a still-image as data is started; and a recording processor that records the still-image as data in accordance with the still-image electronic shutter speed when the light-amount becomes the standard light-amount.

A method for recording a still-image according to an electronic endoscope apparatus including a video-scope with an image sensor, has a steps of: 1) reading image-pixel signals from the image sensor at a still-image electronic shutter speed, which corresponds to a reading time interval shorter than a predetermined time interval defined for displaying a moving-image; 2) controlling a light-amount adjuster for adjusting an amount of light for illuminating a subject, such that the light-amount becomes a standard light-amount corresponding to a recording of the still image, when a series of actions for recording a still-image as data is started; and 3) recording the still-image as data in accordance with the still-image electronic shutter speed when the light-amount becomes the standard light-amount.

BRIEF DESCRIPTION OF THE DRAWINGS

The present invention will be better understood from the description of the preferred embodiments of the invention set fourth below together with the accompanying drawings, in which.

DESCRIPTION OF THE PREFERRED EMBODIMENTS

Hereinafter, the preferred embodiments of the present invention are described with reference to the attached drawings.

Figure 1:
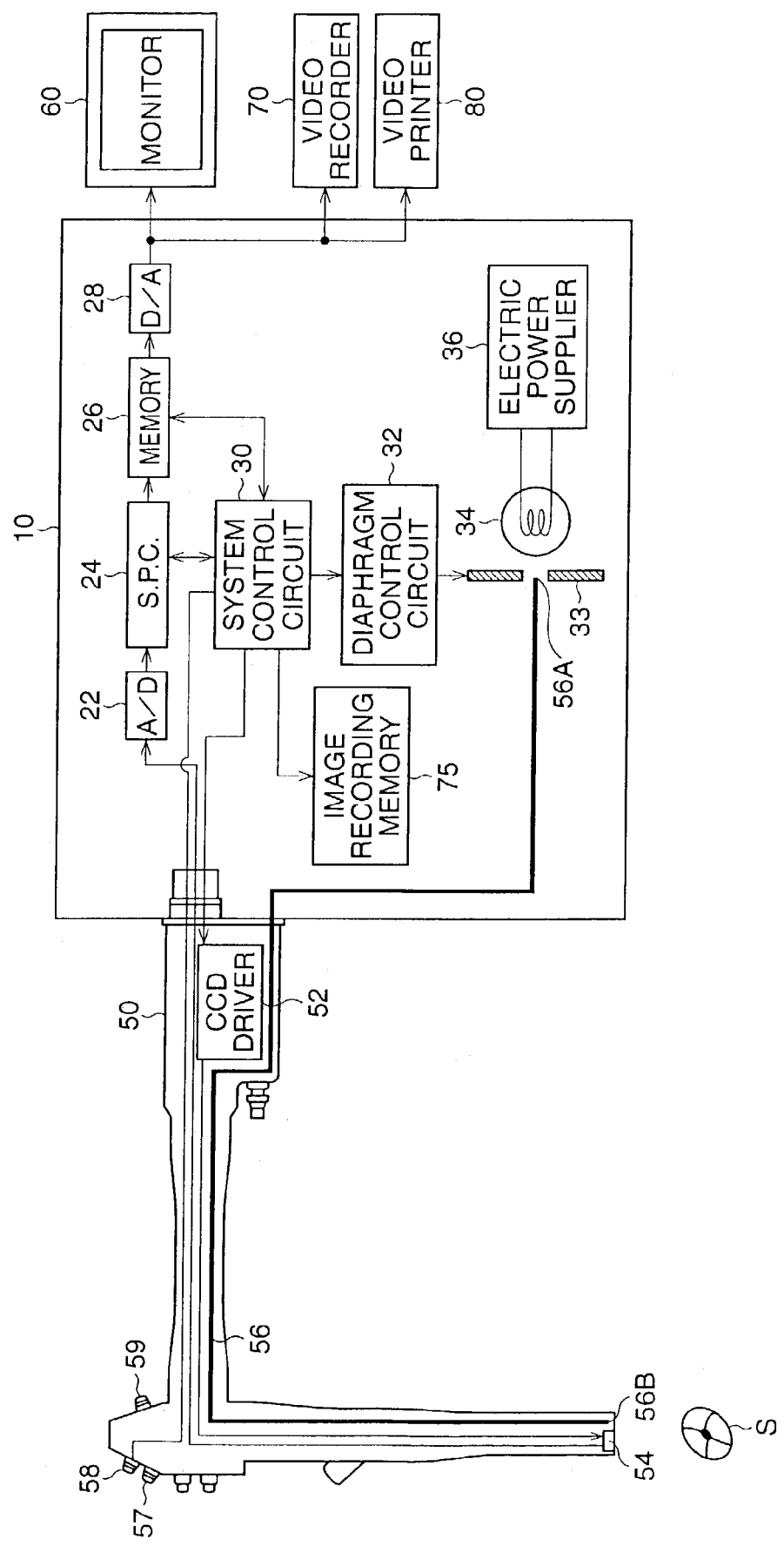
FIG. 1 is a block diagram of an electronic endoscope apparatus according to the first embodiment.

FIG. 1 is a block diagram of an electronic endoscope apparatus according to the first embodiment.

The electronic endoscope apparatus has a video-scope 50 with a CCD (Charge-Coupled Device) 54 and a video-processor 10 that processes image-pixel signals fed from the video-scope 50. The video-scope 50 is detachably connected to the video-processor 10, and further the video-processor 10 is connected to a TV monitor 60, a video recorder 70, and a video printer 80.

When a lamp switch provided on the video-processor 10 (not shown) is turned ON, electric power is supplied from an electric power supplier 36 to a lamp 34, so that light is emitted from the lamp 12 and is directed toward an incident surface 56A of a fiber-optic bundle 56 via a diaphragm 33 and a collecting lens (not shown). The fiber-optic bundle 56, provided through the video-scope 50, directs the light to the distal end of the video-scope 50. The light passing through the fiber-optic bundle 56 exits from an end surface 56B of the fiber-optic bundle 56, and is emitted toward a subject S via a diffusion lens (not shown), so that the subject S is illuminated.

The light reflected on the subject S passes through an objective lens (not shown) and reaches the CCD 54, so that the subject image is formed on a photo-sensor area of the CCD 54. For the color imaging process, in this embodiment, an on-chip color filter method using an on-chip color filter is applied. A color filter (not shown), checkered by four color elements of Yellow (Y), Magenta (Mg), Cyan (Cy), and Green (G), is arranged on the photo-sensor area of the CCD 54 such that the four color elements are opposite to the pixels arranged in the photo-sensor area. Analog image-pixel signals, corresponding to light passing through the color filter, are generated in the CCD 54 by the photoelectric transform effect. The generated color image-pixel signals are composed of plural color signal components. Then, one field worth of image-pixel signals is read from the CCD 54 at regular time intervals in accordance with the so called "color difference line sequential system". In this embodiment, the NTSC standard is used as the color TV standard, accordingly, one field worth of image-pixel signals is read from the CCD 54 at 1/60 second time intervals, and is then fed to the video-processor 10. A CCD driver 52 outputs clock pulses to the CCD 54 to read the image-pixel signals, which are fed to the video-processor 10.

The image-pixel signals are amplified in an amplifier (not shown) and fed to an A/D converter 22, wherein the analog image-pixel signals are converted to digital image signals. The digital image signals are fed to a signal processing circuit 24, wherein an R, G, B gain control process, a gamma correction, and so on, are performed for the digital image signals, and luminance signals are generated from the digital image signals. One field worth of digital image signals is stored in a memory 26, in order, as image-data, whereas the luminance signals are fed to a system control circuit 30 including a CPU (not shown). The digital image signals are output from the memory 26 to a D/A converter 28, in order, wherein the digital image signals are converted to analog image signals. The analog image signals are further converted to video signals, such as NTSC composite signals, in a video processing circuit (not shown) and then fed to the monitor 60, so that the subject image is displayed on the monitor 60 as a "moving-image".

The system control circuit 30 controls the video-processor 10 and outputs control signals to each circuit such as the signal processing circuit 24. A program associated with a control of the video-processor 10 is stored in a ROM (not shown) provided in the system control circuit 30. A timing generator (not shown) outputs clock pulses for adjusting a process-timing for each circuit.

The diaphragm 33, which is provided between the incident surface 56A and the collecting lens, adjusts an amount of light for illuminating the subject S, and it is opened and closed by a diaphragm control circuit 32. The system control circuit 30 outputs control signals to the diaphragm control circuit 32 on the basis of the luminance signals, which are fed from the signal processing circuit 24, in order, such that the brightness of the subject image on the monitor 60 is maintained at a proper brightness. Consequently, driving signals are fed from the diaphragm control circuit 32 to a motor (not shown) and the diaphragm 34, which is connected to the motor, is driven.

A freezing switch button 58 is provided on the video-scope 50. When an operator pushes the freezing switch button 58, an operation signal is fed to the system control circuit 30. Consequently, a normal observation mode for displaying the moving-image is exchanged to a still-image mode, and a series of actions, which produce a called "freeze action", is performed. Namely, as described later, a high-speed electronic shutter action that reads the image-pixel signals at a given high electronic shutter speed, and a recording process for recording, or storing a still-image as data are performed. Thus, one frame worth of digital image signals, corresponding to the still image to be recorded, is temporarily stored in the memory 26 as still-image data.

The one frame worth of digital image signals is recorded in an image recording memory 75, and further fed to the video recorder 70 and the video printer 80 by pushing a recording switch button 57 and a copying switch button 59. Consequently, the still-image is recorded in the video recorder 70, whereas the still-image is printed in the video-printer 80. While the recording process is performed, the digital image signals stored in the memory 26 are not rewritten, so that the still-image is displayed on the monitor 60. When the freezing switch button 58 is pushed again, the freeze action is terminated and the moving-image is displayed on the monitor 60 again.

Figure 2:
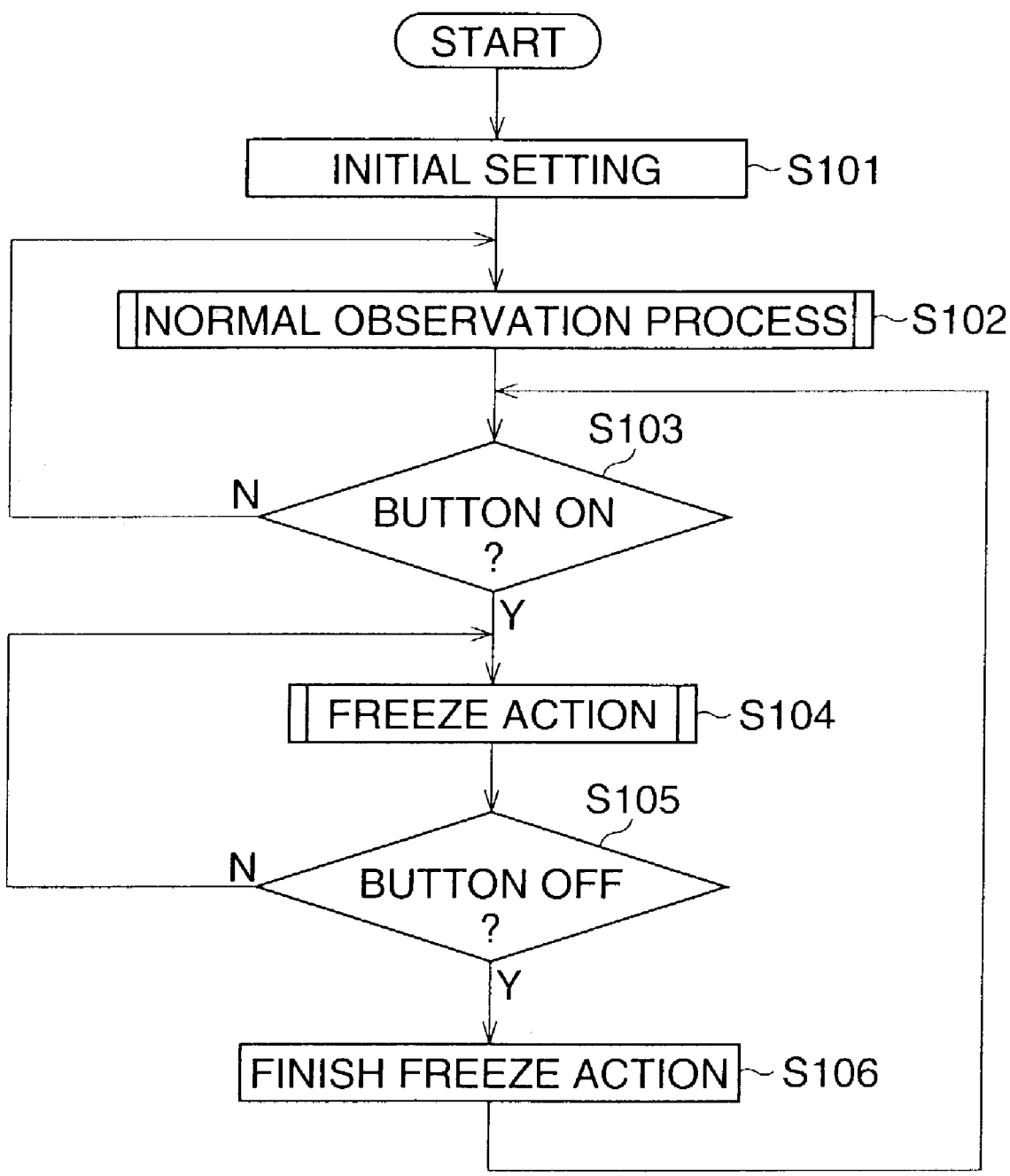
FIG. 2 is a view showing a main routine associated with a video-processor.

FIG. 2 is a view showing a main routine associated with the video-processor 10. When the main electric power is turned ON, the process is started.

In Step S101, a series of parameters, a diaphragm, and so on, are subjected to an initial setting. At this time, the electronic shutter speed for obtaining the still-image as data is also set at a given value. In Step S102, a process according to the normal observation mode is performed. Namely, a process for displaying the moving-image on the monitor 60 is performed. Note that, during the normal observation mode, an automatic light-amount adjusting process, which controls the diaphragm 33 so as to maintain the brightness of the subject image at a proper brightness, is performed. Herein, the automatic light-amount adjusting process is performed at $1/60$ of second time intervals as an interrupt routine. After step S102 is performed, the process goes to Step S103.

In Step S103, it is determined whether the freezing switch button 58 has been depressed, namely, the freezing switch button 58 has been turned ON. When it is determined that the freezing switch button 58 has not been turned ON, the process returns to Step S102. On the other hand, when it is determined that the freezing switch button 58 has been turned ON, the process goes to Step S104. In Step S104, the freeze action is performed so that the still image is obtained and displayed on the monitor 60. At this time, the picture recording action for recording the still-image in video recorder 70 or the copying action for printing the still-image on the video-printer 70 can be performed by pushing the recording switch button 57 or the copying switch button 59. After Step S104 is performed, the process goes to Step S105.

In Step S105, it is determined whether the freezing switch button 58 has been depressed again, namely, the freezing switch button 58 has been turned OFF. When it is determined that the recording switch 58 has not been turned OFF, the process returns to Step S104. On the other hand, when it is determined that the recording switch button 58 has been turned OFF, the process goes to Step S106, wherein the freeze action is terminated so that the moving-image is displayed on the monitor 60 again. After Step S106 is performed, the process returns to Step S103. Steps S102 to S106 are repeatedly performed until the main electric power is turned OFF.

Figure 3:
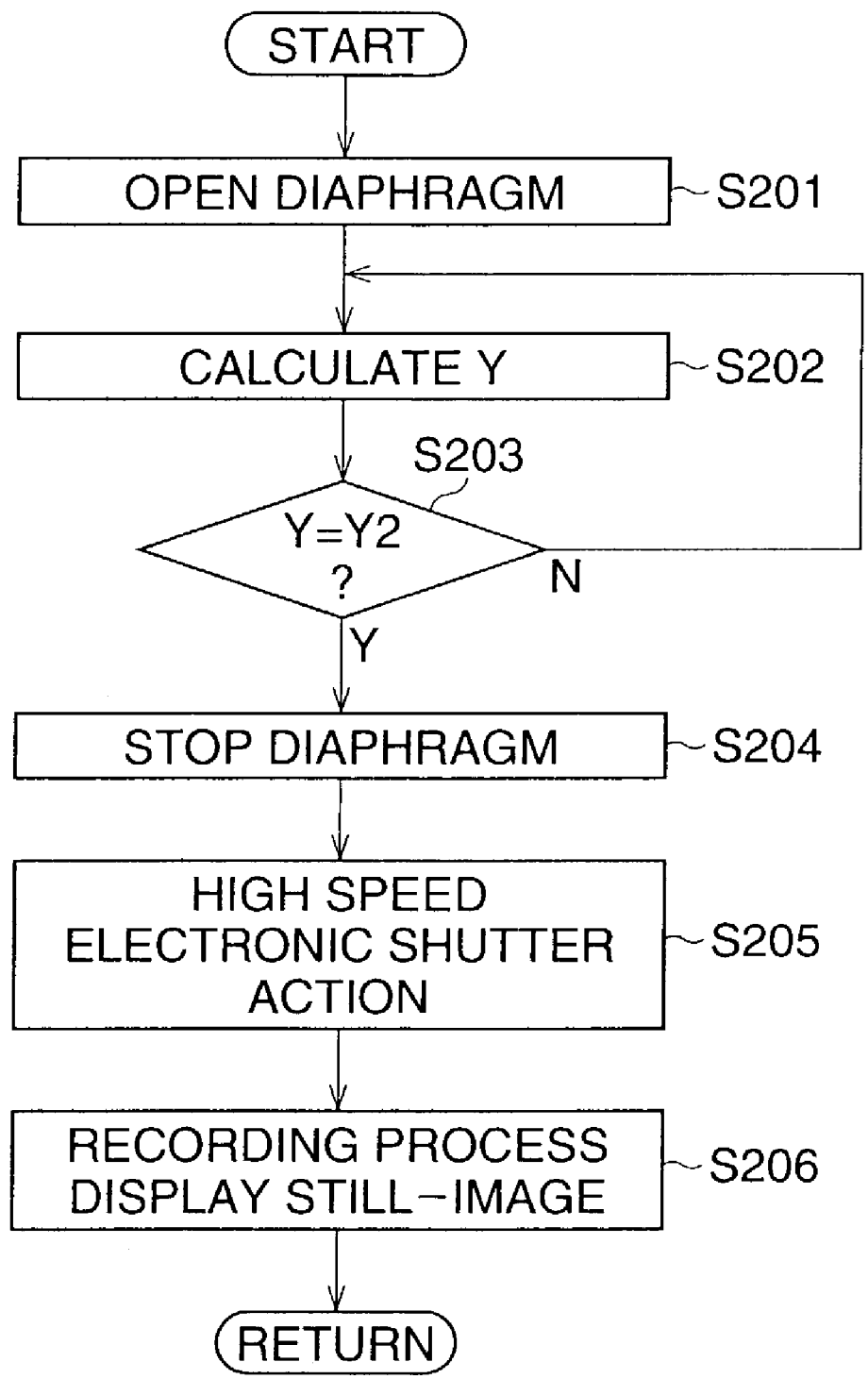
FIG. 3 is a view showing a process associated with a freeze action.
Figure 4:
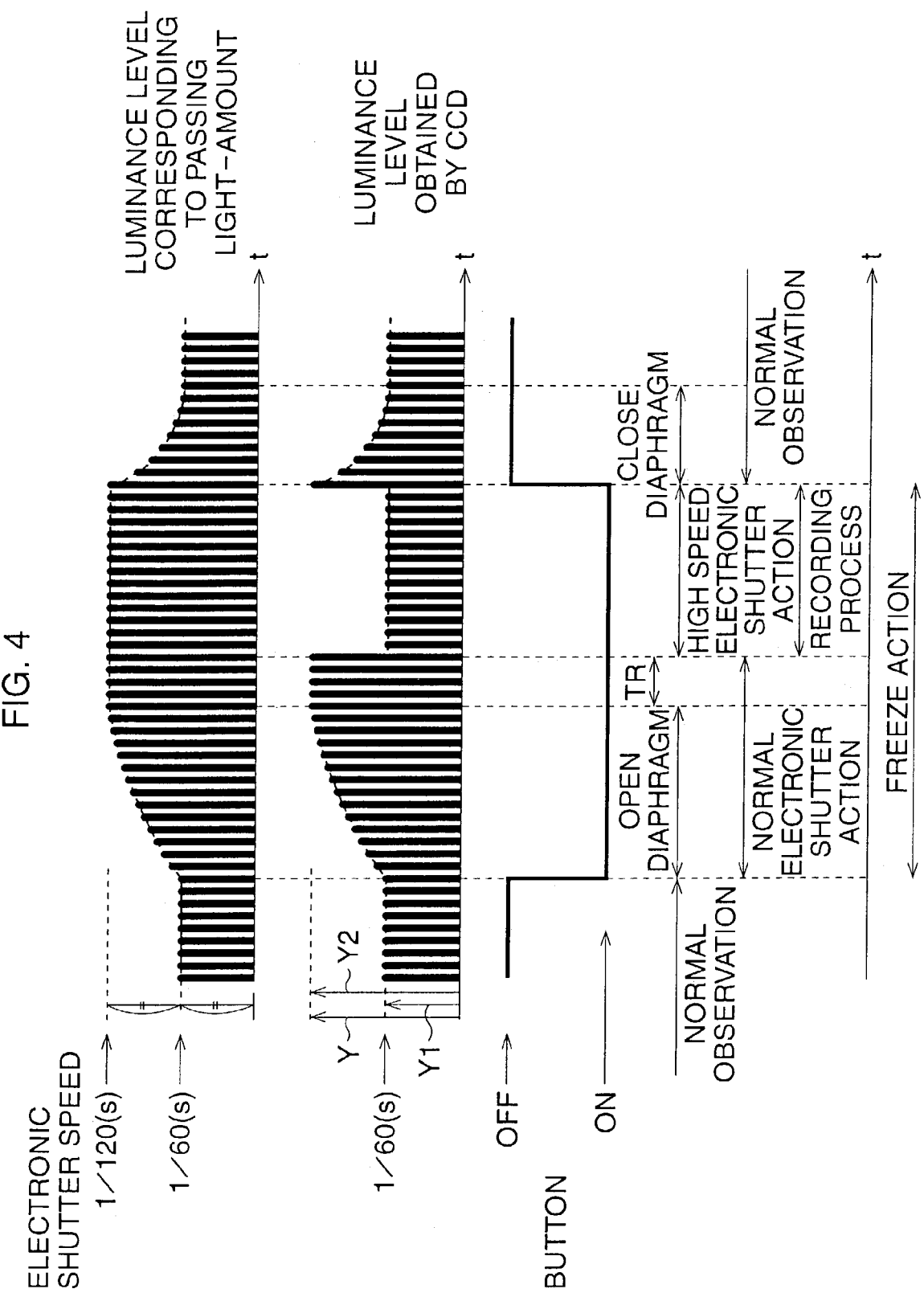
FIG. 4 is a view showing a sequential luminance level during the freeze action.

FIG. 3 is a view showing a subroutine of Step S104 in FIG. 2. FIG. 4 is a view showing a sequential luminance level during the freeze action.

In this embodiment, the light-amount for the subject S is adjusted such that the brightness of the still image substantially coincides with the brightness of the moving-image in normal observation mode. Namely, the light-amount is adjusted such that an amount of accumulated charge in the pixels, which is obtained in still-image mode, substantially coincides with an amount of accumulated charge in the pixels, which is obtained in the normal observation mode. As described above, the image-pixel signals are read from the CCD 54 at $1/60$ of a second time intervals in accordance with the NTSC standard. In other words, the electronic shutter action is performed every $1/60$ of a second. As the amount of the accumulated charges depends upon the electronic shutter speed, the light-amount for the subject S is decided in accordance with the electronic shutter speed. In this embodiment, to record a sharp still image, the electronic shutter speed for the still image is set to "$1/120$" of a second, which is twice the reading time interval ($=1/60$). In other words, the exposed time for the pixels in the CCD 54 is set to half of the exposed time in the normal observation mode. Accordingly, to maintain the brightness of the subject-image at constant brightness regardless of being a still-image or a moving-image, the light-amount for the photo-sensor area of the CCD 54, or the light-amount for the subject S is set to be twice the light-amount immediately before the freeze action.

In FIG. 4, a sequential luminance level, which is detected by the system control circuit 30 in accordance with the luminance signals fed from the signal processing circuit 24, is shown. Further, in FIG. 4, the amount of light that passes the diaphragm 33 (hereinafter, called "passing light amount"), namely, the light-amount for the subject S, is represented by a sequential luminance level. During the normal observation mode, the auto light-amount adjusting process is performed such that the luminance level (hereinafter, represented as a "luminance value Y") of the moving-image is maintained at a proper luminance level indicating a proper brightness of the moving-image (hereinafter, represented as a "moving-image standard luminance value Y1"). Herein, the brightness of the subject image is represented by dividing the brightness range into 256 levels, and the luminance value Y is represented as one integer value among 0 to 255. Note that, the luminance value Y indicates an average luminance value of the subject image, which is obtained by dividing a sum of the product of a given luminance value and the number of corresponding pixels, by the pixel number in one field.

Then, when performing the freeze action, it is determined whether the light-amount for the subject S is twice the light-amount corresponding to the moving-image standard luminance value "Y1", on the basis of the luminance value Y. While determining, the electronic shutter action is performed by $1/60$ of a second. Hereinafter, the luminance value, which has a value twice that of the moving-image standard luminance value Y1, is represented as the "still-image standard luminance value Y2".

In Step S201 in FIG. 3, the control signal is fed from the system control circuit 30 to the diaphragm control circuit 32 so as to further open the diaphragm 33, which is opening with a given opening-degree in the normal observation mode. At this time, the diaphragm 33 is controlled such that the diaphragm 33 opens gradually or step by step. In Step S202, the luminance value Y is sequentially calculated from the one field worth of luminance signals, which are generated in order. While opening the diaphragm 33 and performing the electronic shutter action by the normal electronic shutter speed ($1/60$ of a second), the image-pixel signals are read from the CCD 54 every 1/60 seconds, and the luminance value Y is calculated in accordance with the read image-pixel signals, as shown in FIG. 4. After Step S202 is performed, the process goes to Step S203.

In Step S203, it is determined whether the luminance value Y substantially coincides with the still-image standard luminance value Y2. When it is determined that the luminance value Y does not coincides with the still-image standard luminance value Y2, Step S203 is repeatedly performed until the luminance value Y coincides with the still-image standard luminance value Y2. On the other and, when it is determined that the luminance value Y substantially coincides with the still-image standard luminance value Y2, namely., the light-amount for the subject S is equivalent to a light-amount necessary for the still-image (hereinafter, called a "standard light-amount"), the process goes to Step S204. In Step S204, a control signal is fed to the diaphragm control circuit 32 so as to suspend the opening motion of the diaphragm 33. After Step S204 is performed, the process goes to Step S205.

In Step S205, a control signal is fed from the system control circuit 30 to the CCD driver 52 to perform the recording process, after the delay time TR passed. Namely, the high-speed electronic shutter action with the high electronic shutter speed (=1/120 seconds) is performed. The delay time TR corresponds to a time lag from the outputting of the control signal to the stopping of the diaphragm 33. The CCD driver 52 outputs pulse signals to the CCD 54 to read the accumulated charge such that the exposed time becomes 1/120 of a second. Then, in Step S206, the two field worth of digital image signals obtained using the 1/120 of a second electronic shutter speed, namely, one frame worth of digital image signals are stored in the memory 26. The one frame worth of digital image signals is then recorded in the image recording memory 75 and fed to the video-recorder 70 and the video printer 80 through the memory 26. Since the exposed time during the recording process is a half of that in the normal observation mode, the luminance value Y substantially equals the moving-image standard luminance value Y1 while recording the still-image (See FIG. 4). Further, in Step S206, to display the still image on the monitor 60, the digital image signals stored in the memory 26 are not rewritten during the recording process. After Step S206 is performed, the process is terminated.

In this way, in this embodiment, when the freezing switch button 58 is depressed, the diaphragm 33 is gradually opened such that the light-amount for the subject S becomes the standard light-amount. The high-speed electronic shutter action is not performed until the luminance value Y reaches the still-image standard luminance value Y2. When the luminance value Y coincides with the still-image standard luminance value Y2, the high-speed electronic shutter action and the recording process is performed. Namely, the image-pixel signals are read from the CCD 54 at the high electronic shutter speed (=1/120 second), which is twice the reading time interval corresponding to the NTSC standard (=1/60 second), and the still-image is stored in the memory 26 as data. Then, the still-image stored in the memory 26 is displayed on the monitor 60 and the still-image is recorded in the image recording memory 75. Note that, when the PAL standard, the reading time interval of which are 1/50 of a second, is applied as the TV standard, the electronic shutter speed for recording the still-image is set to 1/100 of a second.

In this embodiment, the electronic shutter speed for recording the still-image is set to twice that of the normal electronic shutter speed (1/60), however, the electronic shutter speed for recording the still-image may be set to a given speed that is capable of producing a still-image with a proper brightness. In this case, the still-image standard luminance value Y2 is set in accordance with the determined electronic shutter speed.

The luminance value Y may be replaced with a value other than the average luminance value, for example, a peak luminance value could be used. Further, when determining whether the light-amount has reached the standard light-amount, the light-amount may be directly detected in place of the use of the luminance value Y obtained by the CCD 54. In this embodiment, one field worth of image-pixel signals is read from the CCD 54 in order, however, one frame worth of image-pixel signals may be read from the CCD 54.

A liquid crystal plate or polarizing plate may be applied to adjust the light-amount, in place of the diaphragm 33. Further, an LED (Light Emitting Diode) may be provided and the light-amount may be adjusted by controlling the amount of light emitted from the LED. In this case, the recording process can be performed immediately after the luminance value Y coincides with the still-image standard luminance value Y2, without the delay time TR.

Figure 5:
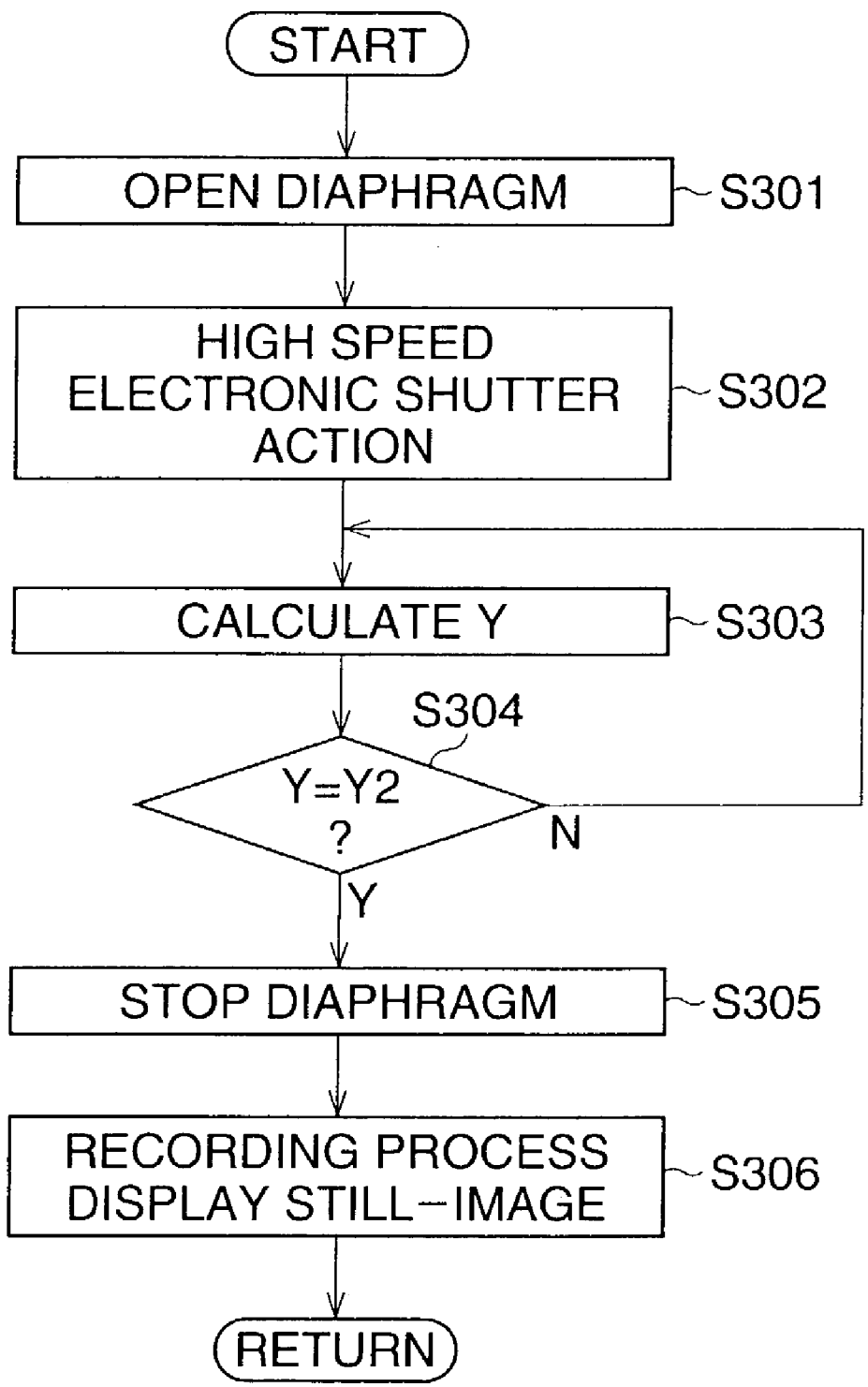
FIG. 5 is a view showing a process associated with the freeze action according to the second embodiment.
Figure 6:
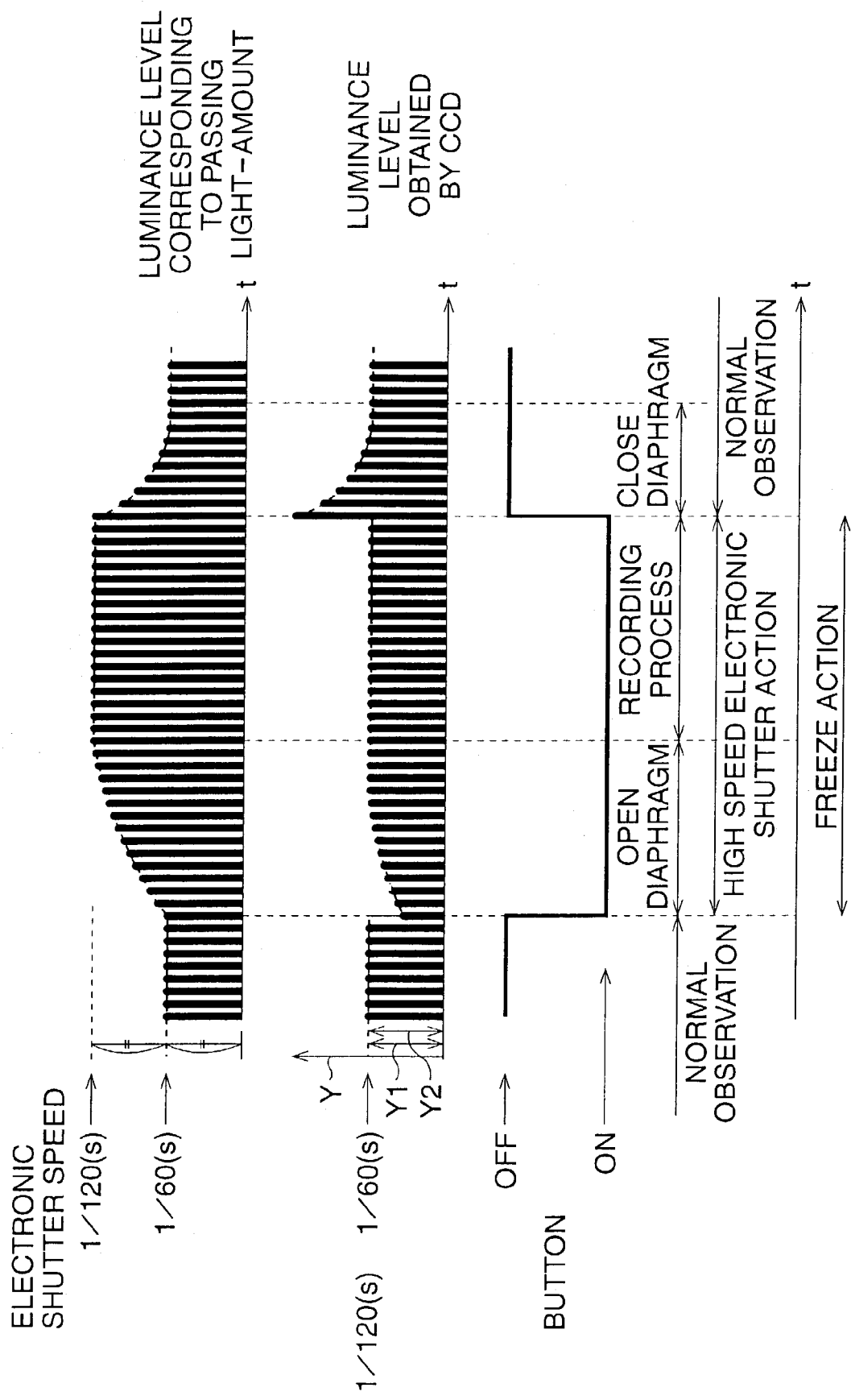
FIG. 6 is a view showing a sequential luminance level during the freeze action according to the second embodiment.

With reference to FIGS. 5 and 6, the second embodiment is explained. The second embodiment is different from the first embodiment in that the high-speed electronic shutter action is performed at the same time that the freeze action is started.

FIG. 5 is a view showing a process associated with the freeze action according to the second embodiment. FIG. 6 is a view showing a sequential luminance level during the freeze action according to the second embodiment.

In Step S301, similarly to Step S201 in FIG. 3, the diaphragm 33 is gradually opened. In Step S302, the high-speed electronic shutter action with the 1/120 of a second electronic shutter speed is performed until the freeze action is finished. Then, in Step S303, similarly to Step 202, the luminance value Y is calculated from the image signals. Since the high-speed electronic shutter action is performed at the same time as the opening action of the diaphragm 33, the luminance value Y instantaneously becomes a half of the moving-image standard luminance value Y1. The luminance value Y gradually increases as the diaphragm 33 gradually opens (See FIG. 6). Herein, the still-image standard luminance value Y2 is the same as the moving-image standard luminance value Y1.

In Step S304, similarly to Step S203, it is determined whether the luminance value Y substantially coincides with the still-image standard luminance value Y2. When it is determined that the luminance value Y does not coincide with the still-image standard luminance value Y2, the process returns to Step S303. On the other hand, when it is determined that the luminance value Y substantially coincides with the still-image standard luminance value Y2, the process goes to Step S305. The process in Step S305 and S306 are the same as the process in Step S204 and S206 in FIG. 3. Namely, the opening action of the diaphragm 33 is stopped, the recording process is performed, and the still-image is displayed on the monitor 60.

In this way, in the second embodiment, when the freezing switch button 58 is depressed, the diaphragm 33 is driven and the high-speed electronic shutter action is performed at the same time. Then, when the luminance value Y coincides with the still-image standard luminance value Y2, the recording process is performed.

Figure 7:
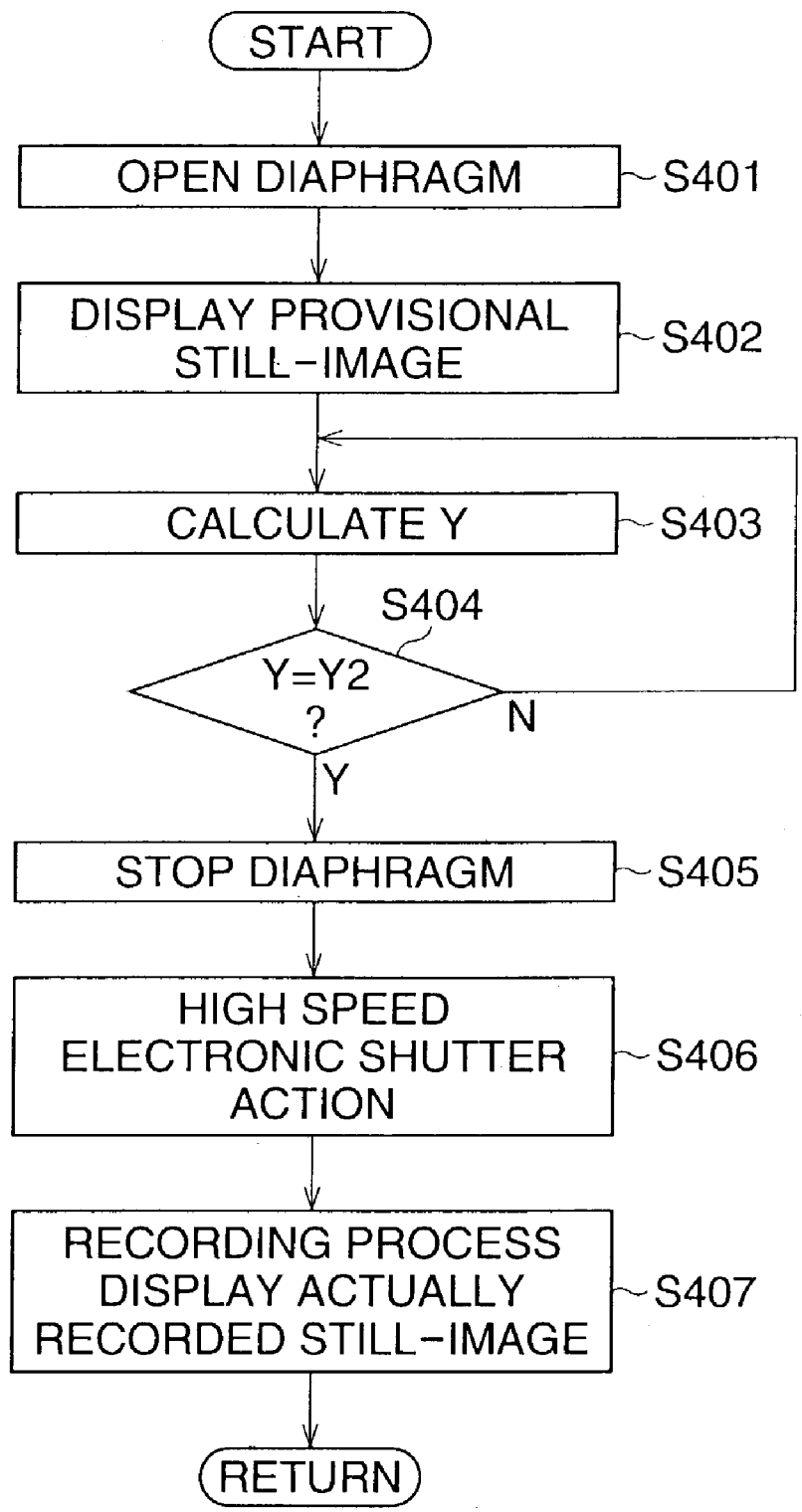
FIG. 7 is a view showing a process associated with the freeze action according to the third embodiment.
Figure 8:
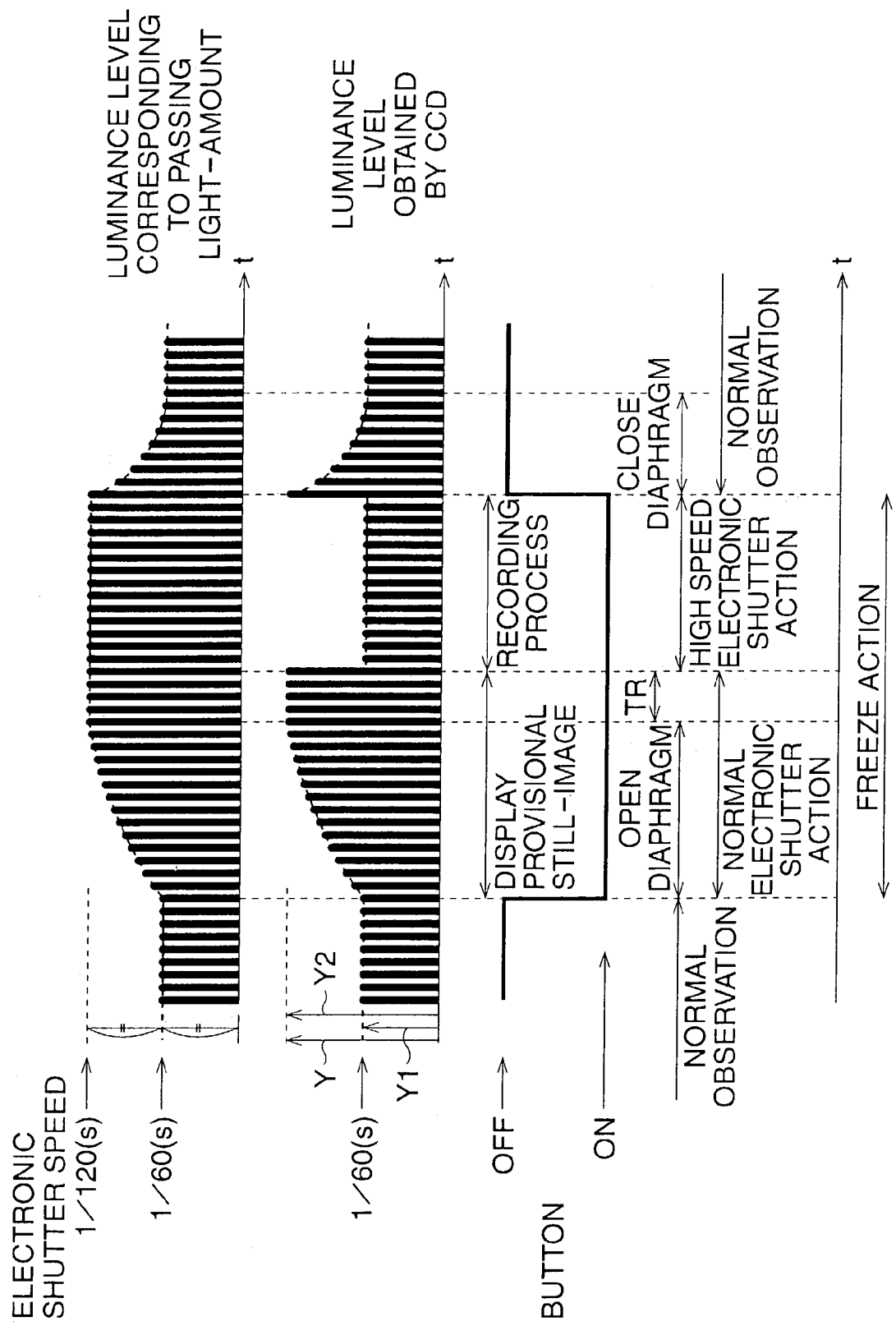
FIG. 8 is a view showing a sequential luminance level during the freeze action according to the third embodiment.

With reference to FIGS. 7 and 8, the third embodiment is explained. The third embodiment is different from the first embodiment in that a still-image is provisionally displayed when the freeze action is started.

FIG. 7 is a view showing a process associated with the freeze action according to the third embodiment. FIG. 8 is a view showing a sequential luminance level during the freeze action according to the third embodiment.

In Step S401, similarly to Step S201 in FIG. 3, the diaphragm 33 is gradually opened. In Step S402, a provisional display process is performed. Namely, to provisionally display a still-image, one frame worth of digital image signals is stored in the memory 26. At this time, the electronic shutter action is performed at 1/60 of a second corresponding to the normal observation mode. Once the digital image signals are stored in the memory 26 as provisional still-image data, the memory 26 is not rewritten until the recording process is performed. Consequently, a provisional still-image is displayed on the monitor 60. The brightness of the displayed provisional still-image does not change remarkably compared to the brightness of the moving-image immediately before Step S401 is performed.

The performance of Steps S403 to S406 respectively corresponds to the performance of Steps S202 to S205 in FIG. 3. Namely, the luminance value Y is calculated, and it is determined whether the luminance value Y coincides with the still-image standard luminance value Y2. When it is determined that the luminance value Y coincides with the still-image standard luminance value Y2, the opening action of the diaphragm 33 is stopped and the high-speed electronic shutter action is performed.

In Step S407, the recording process is performed. Further, the provisional still-image stored in the memory 26 is renewed and the actual recorded still-image, photographed at 1/120 of a second electronic shutter speed, is displayed on the monitor 60. After Step S407 is performed, this process is terminated.

In this way, in the third embodiment, when the freezing switch button 58 is turned ON, the digital image signals for the provisional still-image are stored in the memory 26. Then, the provisional still-image is displayed on the monitor 60 until the actual recorded still-image is displayed. Thus, the brightness of the displayed subject image does not abruptly change with respect to the moving-image immediately before the freeze action is started.

Figure 9:
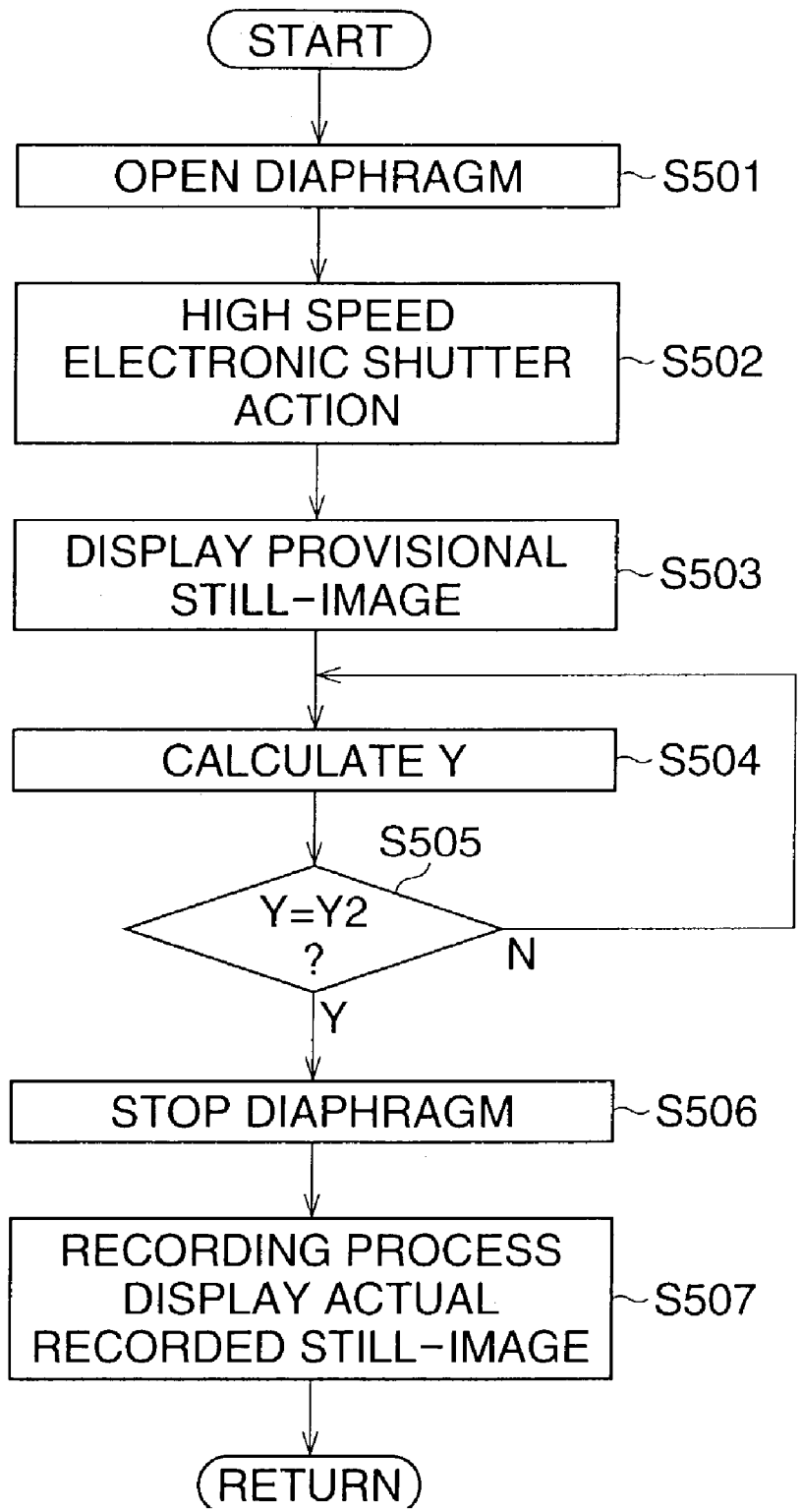
FIG. 9 is a view showing a process associated with the freeze action according to the fourth embodiment.
Figure 10:
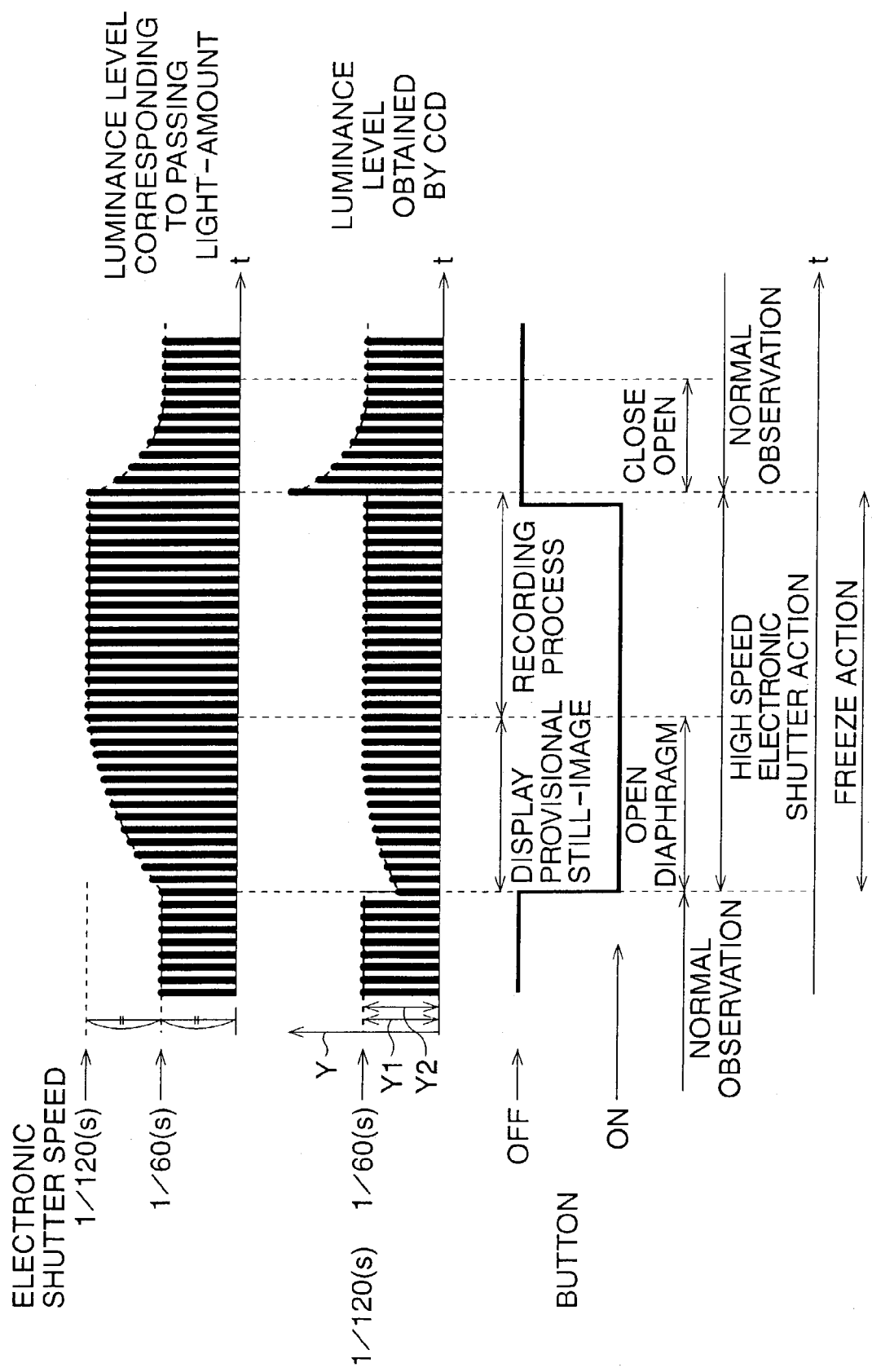
FIG. 10 is a view showing a sequential luminance level during the freeze action according to the fourth embodiment.

With reference to FIGS. 9 and 10, the fourth embodiment is explained. The fourth embodiment is different from the third embodiment in that the high-speed electronic shutter action is performed at the same time that the freeze action is started, similarly to the second embodiment.

FIG. 9 is a view showing a process associated with the freeze action according to the fourth embodiment. FIG. 10 is a view showing a sequential luminance level during the freeze action according to the fourth embodiment.

The performance of Steps S501 and S502 respectively corresponds to Steps S301 and S302 in FIG. 5. Namely, the diaphragm 33 is gradually opened, and the high-speed electronic shutter action is performed. In Step S503, similarly to Step S402 in FIG. 7, to provisionally display a still image, one frame worth of digital image signals are stored in the memory 26 as provisional still-image data, and the memory 26 is not rewritten until the recording process is performed, so that a provisional still-image is displayed on the monitor 60. The performance of Steps S504 to S506 respectively corresponds to the performances of Steps S303 to S305 in FIG. 5. Namely, the luminance value Y is calculated, and it is determined whether the luminance value Y coincides with the still-image standard luminance value Y2. When it is determined that the luminance value Y coincides with the still-image standard luminance value Y2, the opening action of the diaphragm 33 is stopped. In Step S507, similarly to Step S407 in FIG. 7, the recording process is performed, namely, the provisional still-image stored in the memory 26 is renewed and the actual recorded still-image is displayed on the monitor 60. After Step S507 is performed, this process is terminated.

With reference to FIGS. 11 to 14, the fifth embodiment is explained. The fifth embodiment is different from the first, second, third, and fourth embodiments in that the shift-amount of the diaphragm in the freeze action is predetermined.

Figure 11:
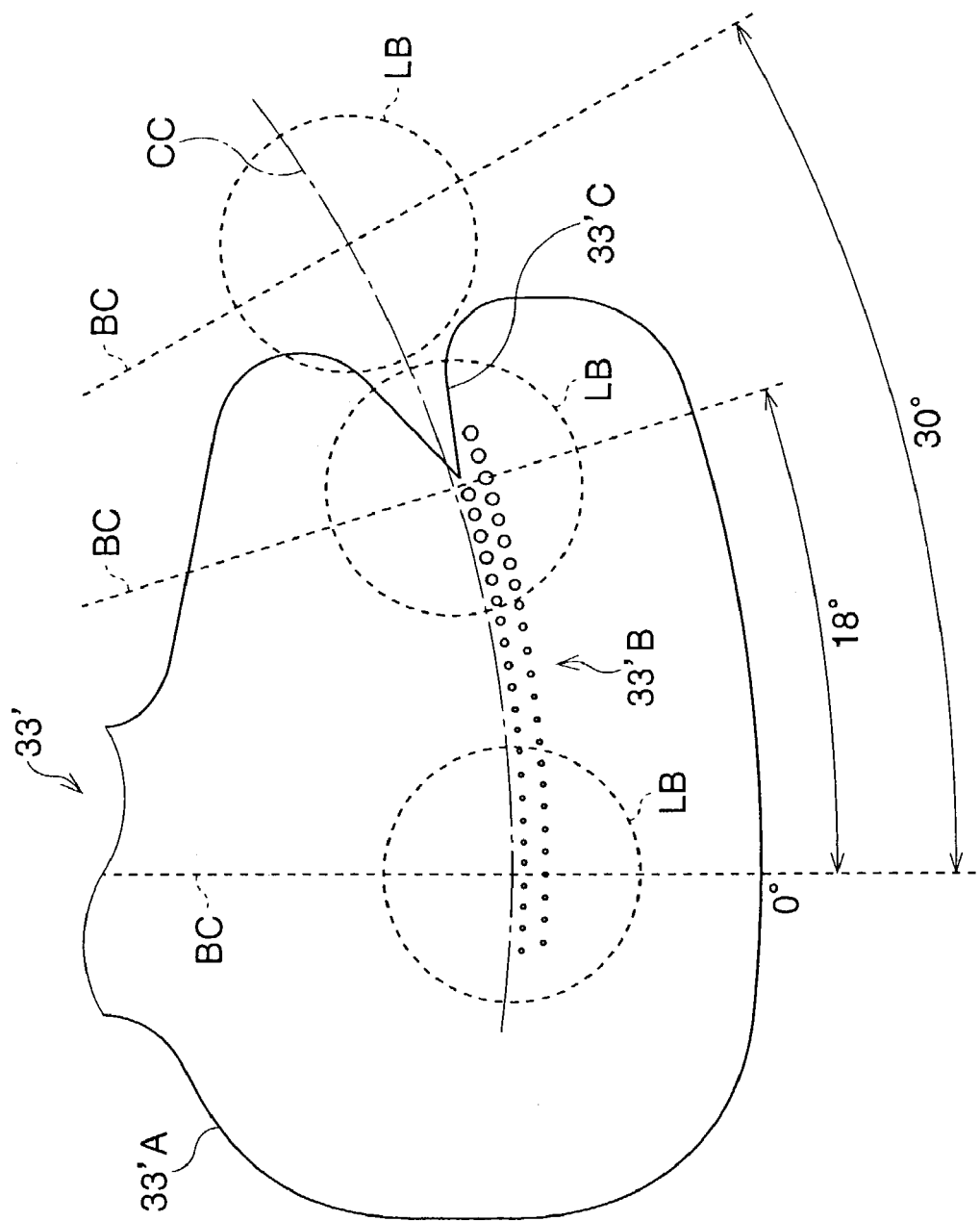
FIG. 11 is a schematic front view of a diaphragm according to the fifth embodiment.
Figure 12:
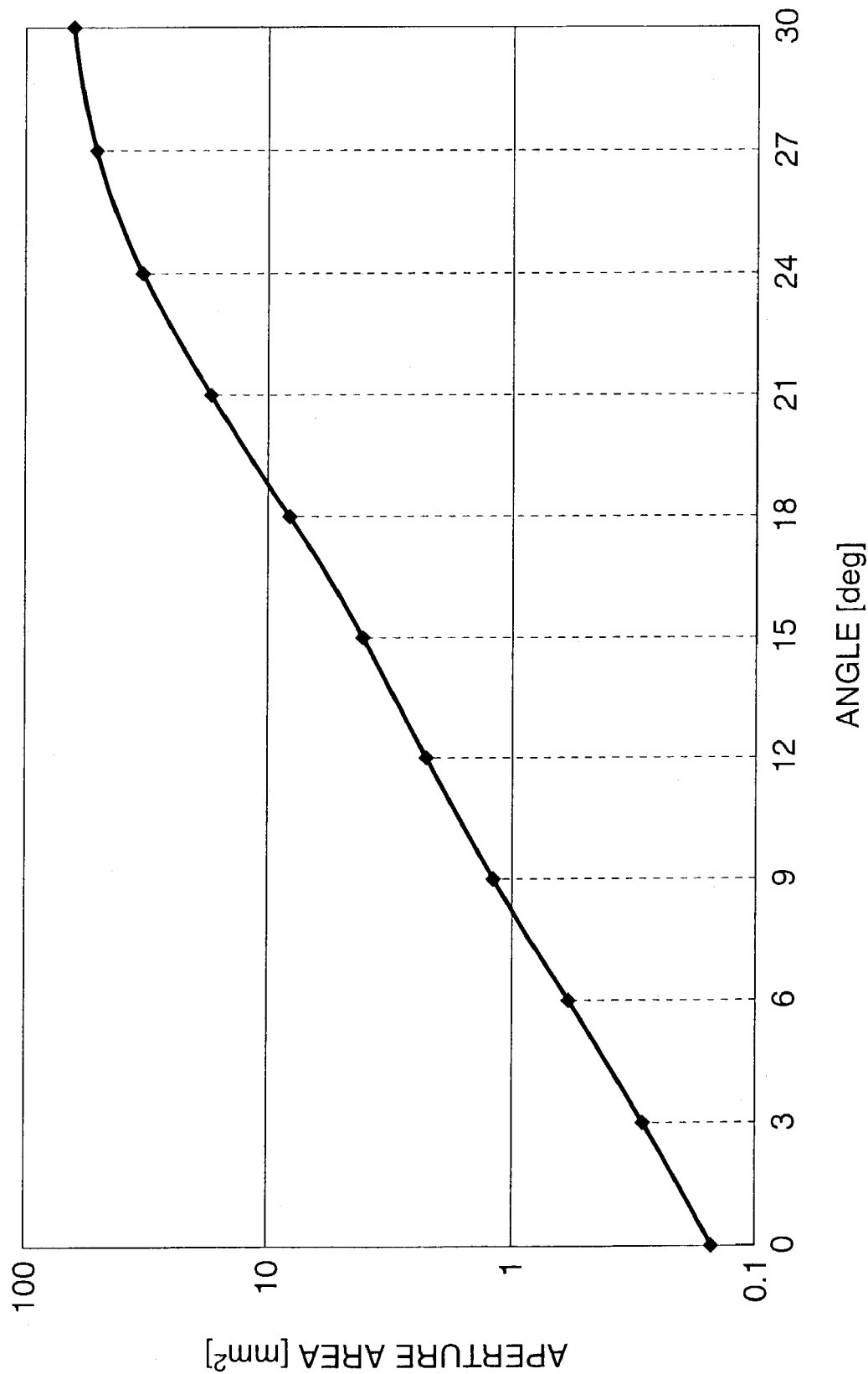
FIG. 12 is a view showing a logarithmic graph, in which the aperture characteristics associated with the diaphragm are represented.

FIG. 11 is a schematic front view of a diaphragm according to the fifth embodiment. FIG. 12 is a view showing a logarithmic graph exhibiting the aperture characteristics of the diaphragm.

The diaphragm 33' according to the fifth embodiment is constructed of an insulating member 33'A, which has a size larger than the luminous flux "LB" of light passing from the lamp 34 toward the incidence surface 56A of the fiber-optic bundle 56 (shown in FIG. 1), and an arm (not shown) for supporting the insulating member 33'A. An end portion of the arm is mechanically connected to the motor, which is connected to the diaphragm control circuit 32 shown in FIG. 1, and the diaphragm 33' pivots around the end portion of the arm in accordance with the rotation of the motor. Consequently, the insulating member 33'A continuously moves along an arc "CC". A line "BC", which connects the center of the luminous flax "LB" and the pivot axis of the end portion of the arm, represents a standard line for defining the angle of the diaphragm 33'. The diaphragm 33' shifts between 0 to 30 degrees. In FIG. 3, the relative position-relationship between the diaphragm 33' having angles of 0, 18, and 30 degree and the luminous flax "LB" is represented. A notch 33'C is formed on the insulating member 33'A, and a lot of minute holes 33B are formed along the arc "CC".

In this embodiment, the relationship between the aperture area of the diaphragm 33', corresponding to the light-amount for the subject S, and the angle of the diaphragm 33', can be represented by the exponential functions. Therefore, when the relationship between the angle and the aperture area is represented by a logarithmic graph, as shown in FIG. 12, the linear relationship is generally maintained. Namely, as the angle increases by a given-amount, the aperture area increases by a constant factor. The plural holes 33'B and the notch 33'A are formed on the insulating member 33'A so that the linear relationship shown in FIG. 12 is maintained. Herein, the aperture area increases so that light-amount doubles every time the diaphragm 33' opens by 3 degrees.

Figure 13:
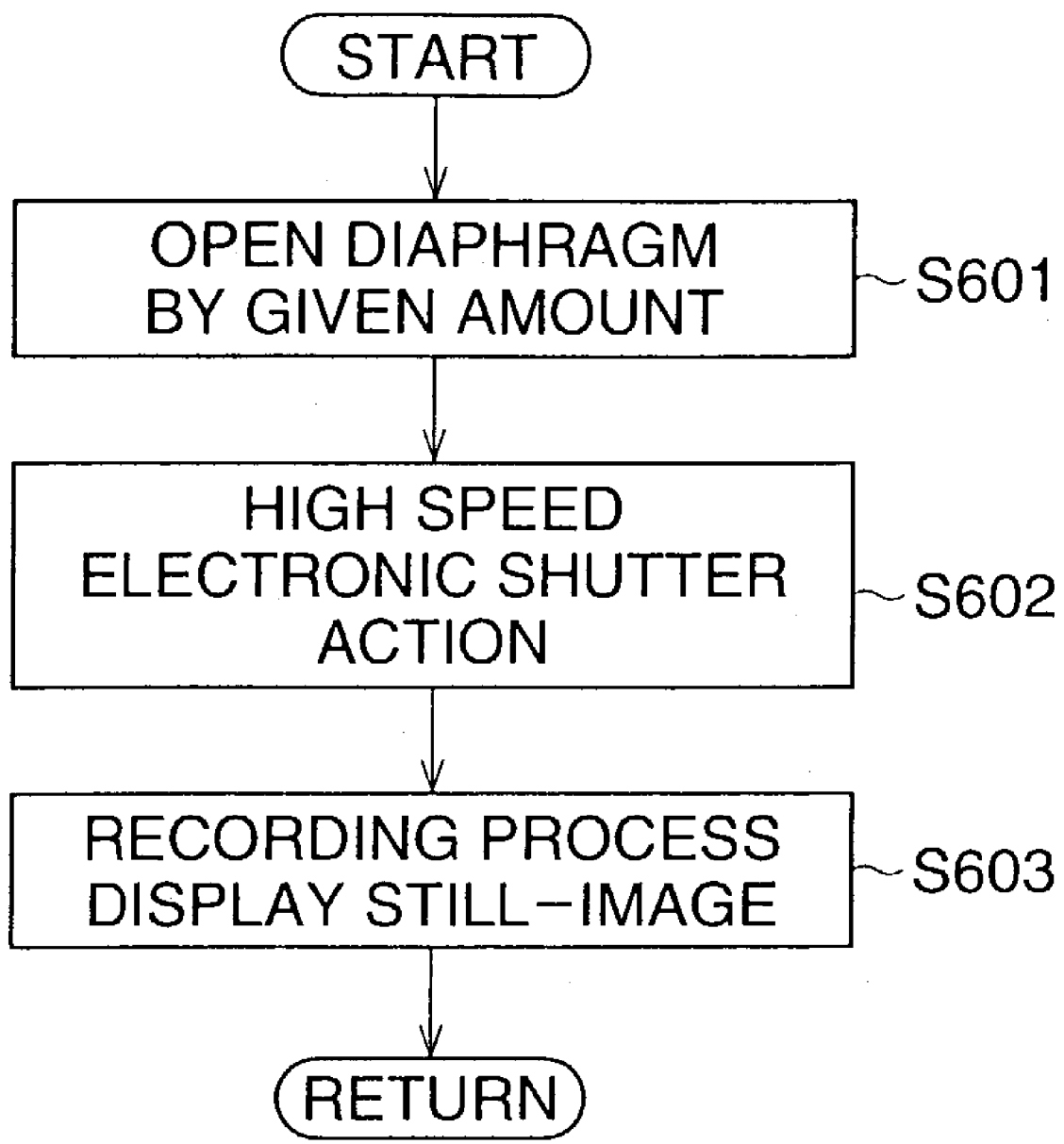
FIG. 13 is a view showing a process associated with the freeze action according to the fifth embodiment.
Figure 14:
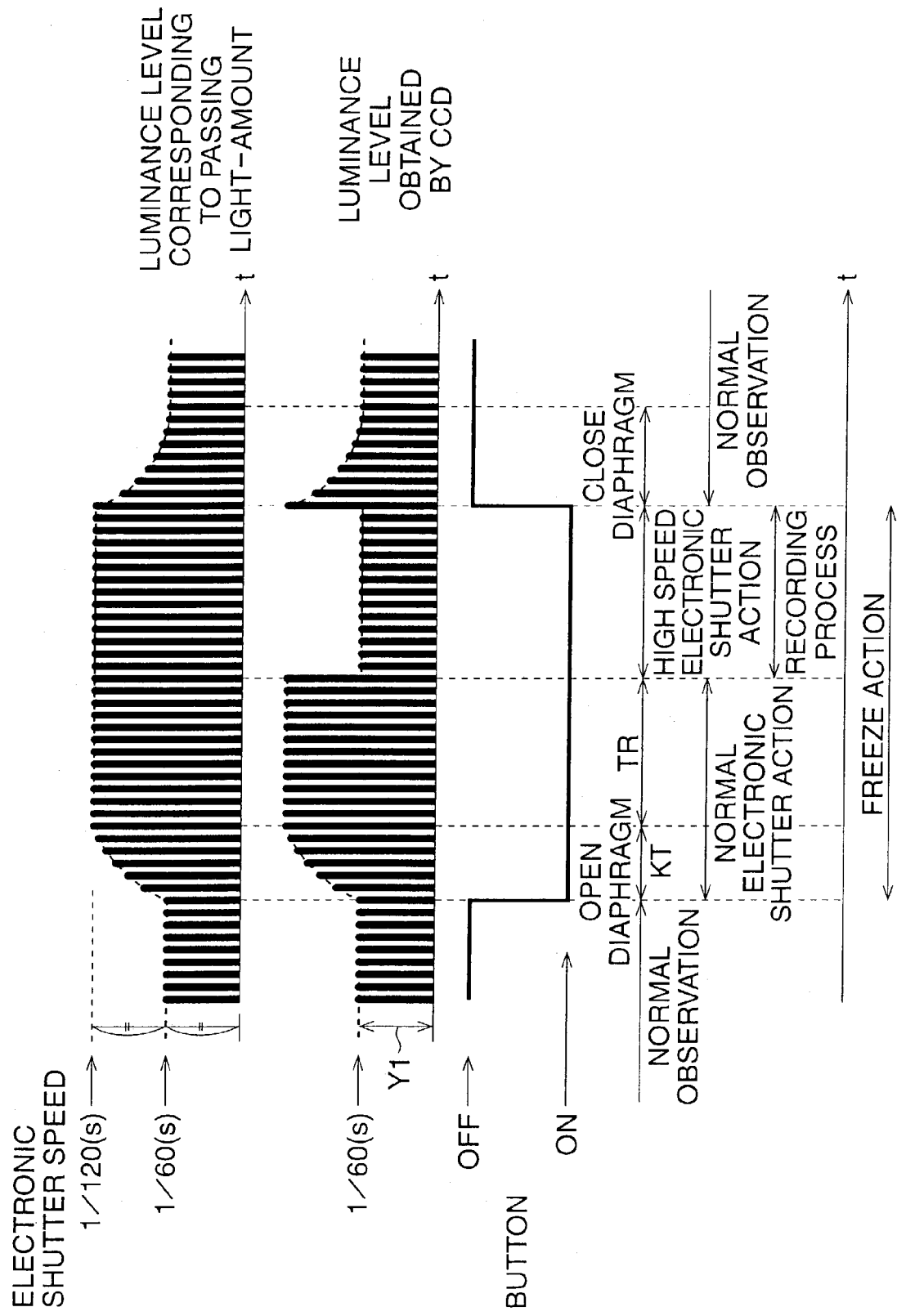
FIG. 14 is a view showing a sequential luminance level during the freeze action according to the fifth embodiment.

FIG. 13 is a view showing a process associated with the freeze action according to the fifth embodiment. FIG. 14 is a view showing a sequential luminance level during the freeze action according to the fifth embodiment.

As described above, the aperture area of the diaphragm 33' doubles every time the diaphragm 33' opens by 3 degrees. Namely, the light-amount for the subject S doubles every time the diaphragm 33' opens by 3 degrees. Accordingly, when the freezing switch button 58 is depressed, the diaphragm 33' is driven so that the diaphragm 33' further opens by 3 degrees relative to the present angle in the normal observation mode.

In Step S601, a control signal is fed to the diaphragm control circuit 32 to further open the diaphragm 33' by 3 degrees as described above. In Step S602, the high-speed electronic shutter action is performed immediately after a driving time KT and the delay time TR has passed. The driving time KT indicates a time for actually opening the diaphragm 33' by 3 degrees. The delay time TR indicates a time from actually opening the diaphragm 33' by 3 degrees to completely stopping the diaphragm 33' by the control signal to suspend the opening motion. In Step S603, similarly to Step S206 in FIG. 3, the recording process is performed and the still-image is displayed on the monitor 60.

In this way, in the fifth embodiment, when the freezing switch button 58 is turned ON, the diaphragm 33' opens by 3 degrees such that the light-amount for the subject S becomes twice the light-amount for the normal observation mode corresponding to the moving-image standard luminance value Y1, namely, the standard light-amount. When performing the freeze action, the diaphragm 33' is always opened by 3 degrees regardless the present opening-degree. Accordingly, the response time for driving the diaphragm 33' is always constant, so that the freeze action is rapidly and smoothly performed.

Figure 15:
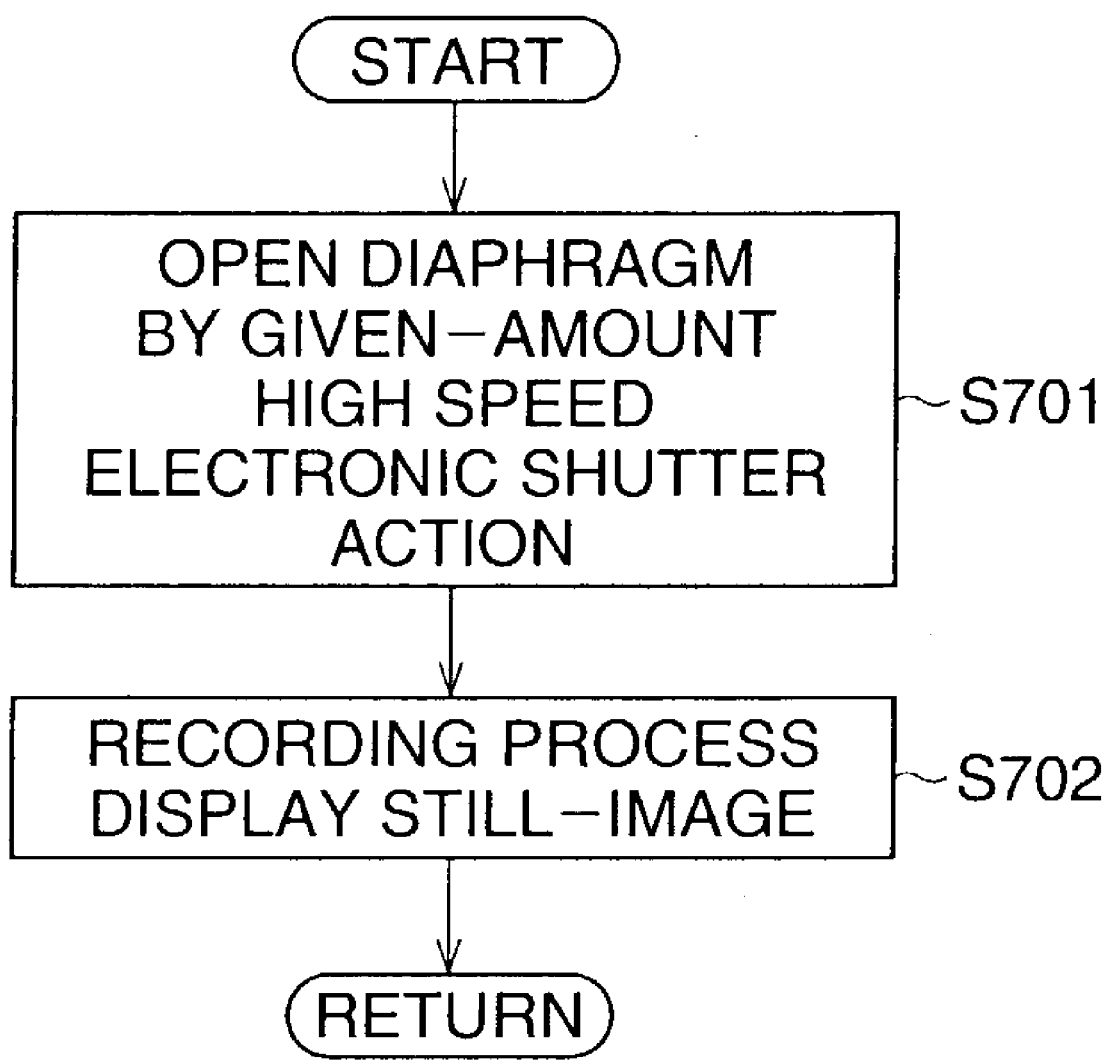
FIG. 15 is a view showing a process associated with the freeze action according to the sixth embodiment.
Figure 16:
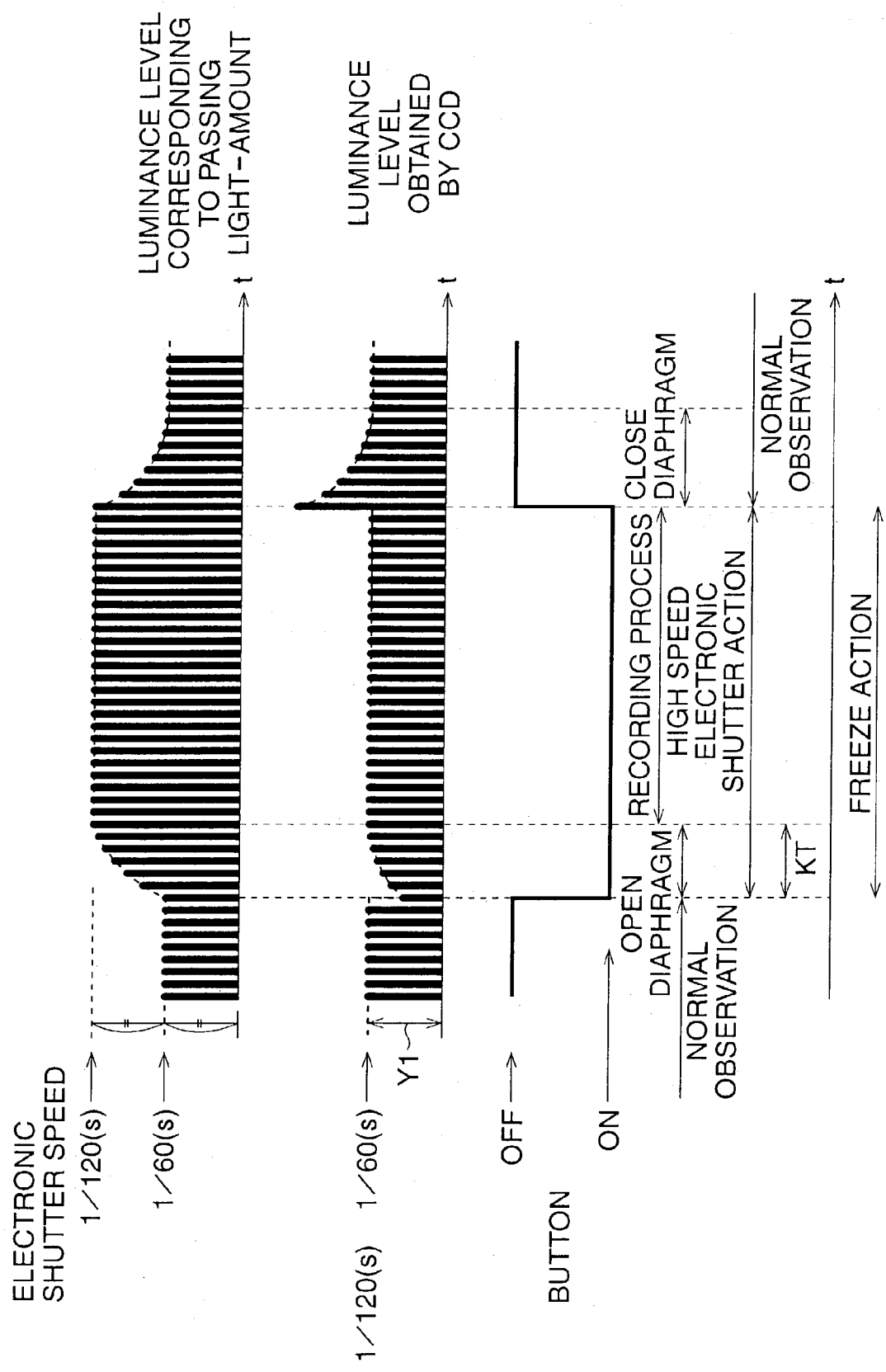
FIG. 16 is a view showing a sequential luminance level during the freeze action according to the sixth embodiment.

With reference to FIGS. 15 and 16, the sixth embodiment is explained. The sixth embodiment is different from the fifth embodiment in that the high-speed electronic shutter action is performed immediately after the freeze action is started, similarly to the second and fourth embodiments.

FIG. 15 is a view showing a process associated with the freeze action according to the sixth embodiment. FIG. 14 is a view showing a sequential luminance level during the freeze action according to the sixth embodiment.

In Step 701, the diaphragm 33' is driven by 3 degrees and the high-speed electronic shutter action is performed immediately after the freeze action is started. Then, in Step S702, the recording process is performed after the driving time KT has passed, and the still-image is displayed on the monitor 60.

Figure 17:
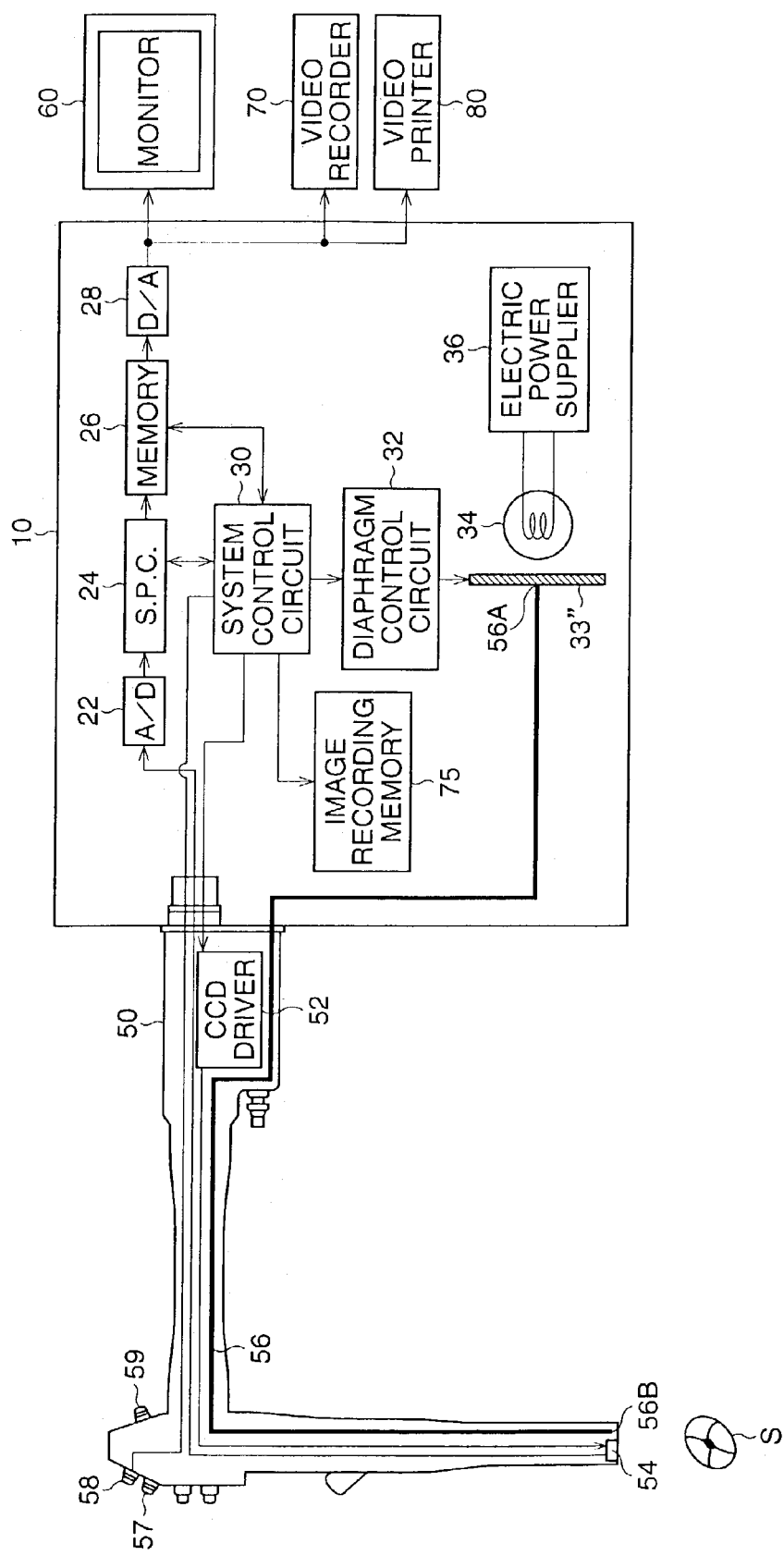
FIG. 17 is a block diagram of the electronic endoscope apparatus according to the seventh embodiment.
Figure 18:
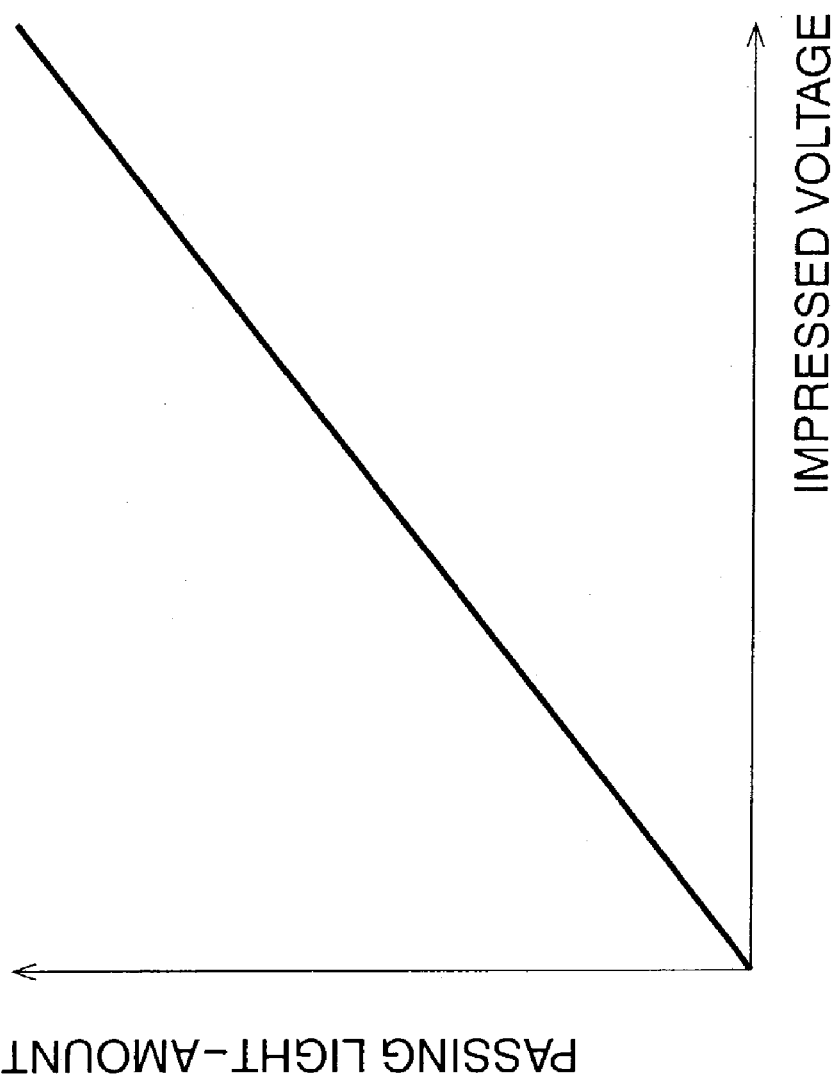
FIG. 18 is a view showing a relationship between the impressed voltage and the passing light-amount.

With reference to FIGS. 17 and 18, the seventh embodiment is explained. The seventh embodiment is different from the fifth and sixth embodiments in that a liquid crystal shutter is used in place of the diaphragm.

FIG. 17 is a block diagram of the electronic endoscope apparatus according to the seventh embodiment. FIG. 18 is a view showing a relationship between the impressed voltage and the passing light-amount.

As shown in FIG. 17, a liquid crystal plate 33" is provided between the incidence surface 56A of the fiber-optic bundle 56 and the lamp 34. The liquid crystal plate 33" functions as a liquid crystal shutter, which adjusts the passing light-amount that passes through the liquid crystal plate 33", namely, the light-amount for the subject S, by changing the molecular arrangement of the crystal. FIG. 18 shows a logarithmic graph, wherein the relationship between an impressed voltage for the liquid crystal plate 33" and the passing light-amount is indicated. As shown in FIG. 18, the linear relationship is maintained between the impressed voltage and the passing light-amount. Accordingly, when the freeze action is started, similarly to the fifth and sixth embodiments, the impressed voltage of the liquid crystal plate 33" is controlled by a predetermined change voltage-amount, which is necessary for achieving the standard light-amount.

Figure 19:
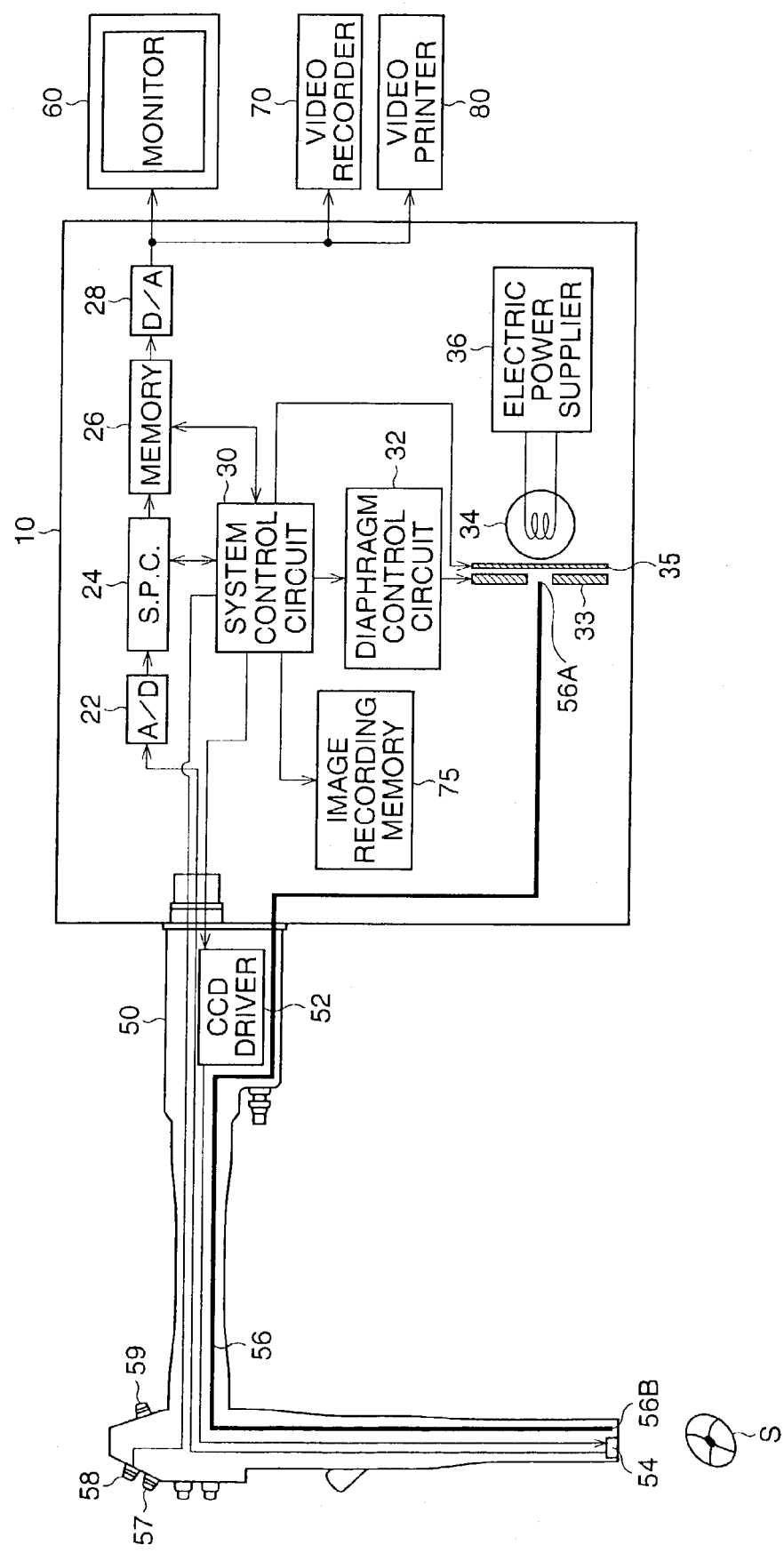
FIG. 19 is a block diagram of the electronic endoscope apparatus according to the eighth embodiment.
Figure 20:
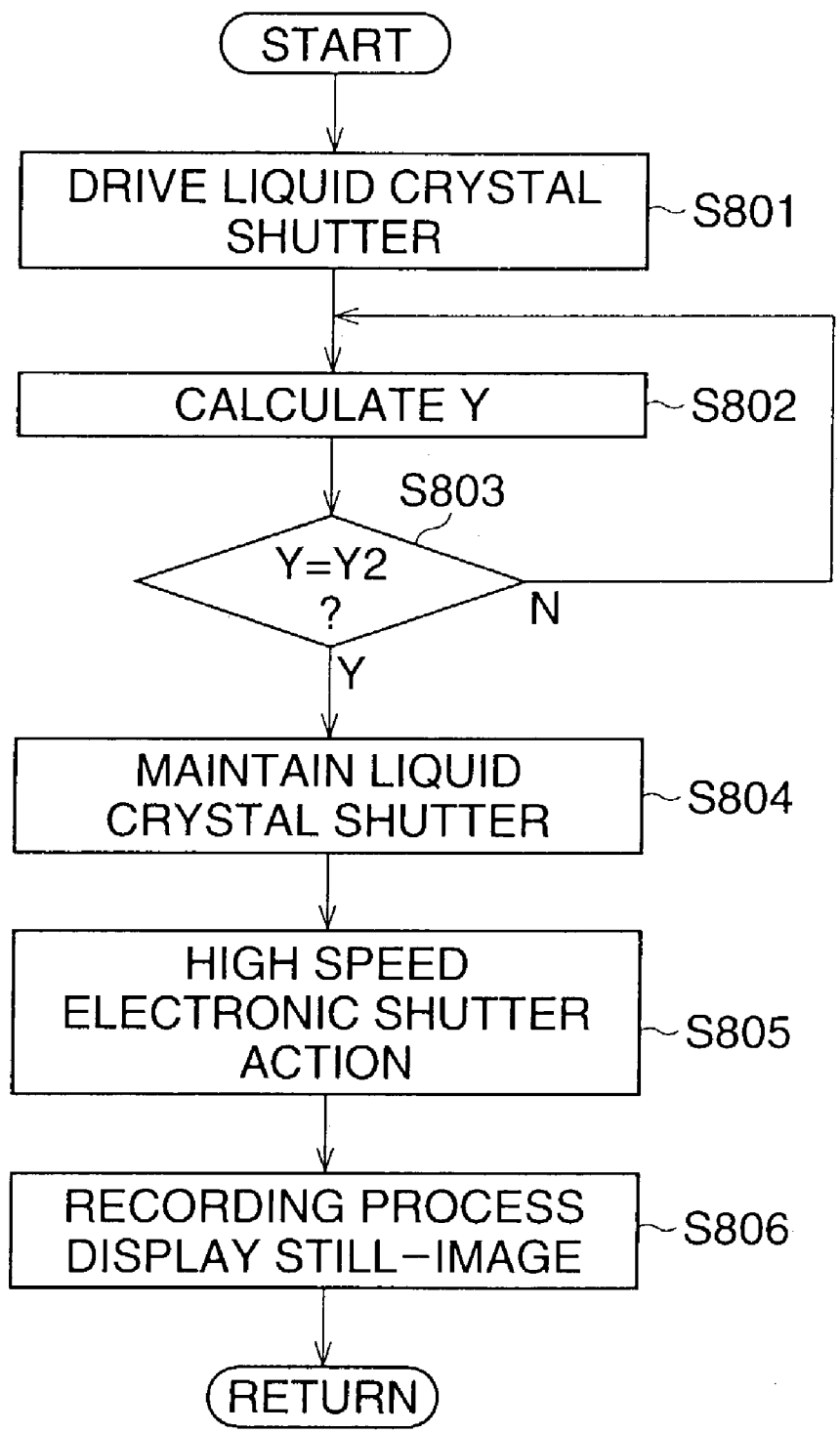
FIG. 20 is a view showing a process associated with the freeze action according to the eighth embodiment.
Figure 21:
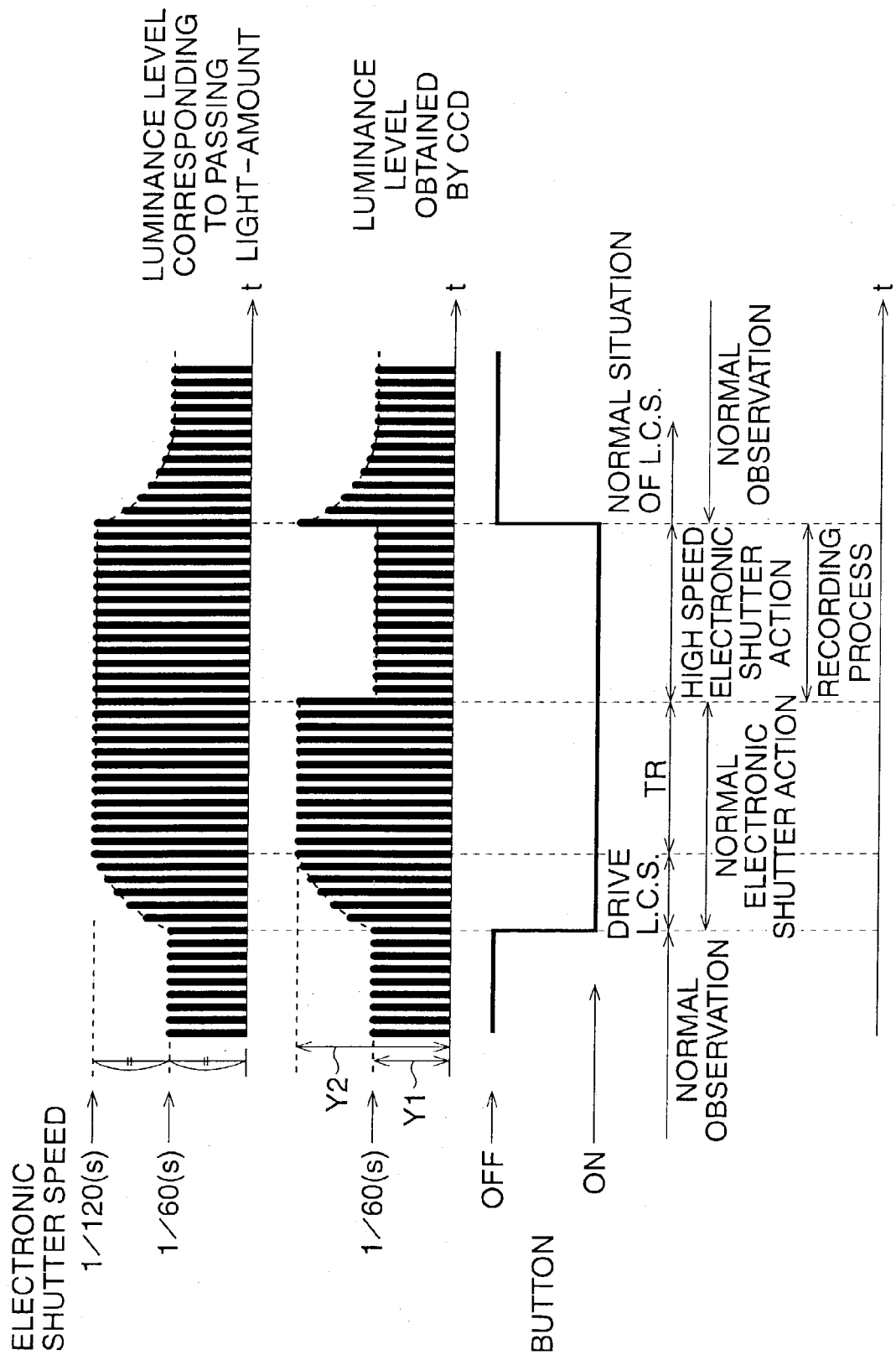
FIG. 21 is a view showing a sequential luminance level during the freeze action according to the eighth embodiment.

With reference to FIGS. 19 to 21, the eighth embodiment is explained. The eights embodiment is different from the first embodiment in that a liquid crystal shutter is further provided for adjusting the light-amount, in addition to a diaphragm.

FIG. 19 is a block diagram associated with the electronic endoscope apparatus according to the eighth embodiment.

A liquid crystal shutter 35 is provided between the diaphragm 33 and the lamp 34, and adjusts the light-amount for the subject by increasing and decreasing the amount of passing light. The liquid crystal shutter 35 is driven by a control signal fed from the system control circuit 30. When the control signal is output from the system control circuit 30, a liquid crystal driver (not shown) drives the liquid crystal shutter 35. During the normal observation mode, the liquid crystal shutter passes a light having a predetermined intensity so that a constant light-amount is directed toward the diaphragm 33. Speaking concretely, the light that enters into the liquid crystal shutter 35 is diffused in accordance with a molecular arrangement situation in the liquid crystal shutter 35, so that the intensity of the light that passes through the liquid crystal shutter 35 is decreased and the light-amount for the subject S is decreased. When performing the freeze action, the molecular arrangement situation changes so as to increase the intensity of the passing light, so that the light-amount for the subject S increases.

FIG. 20 is a view showing a process associated with the freeze action according to the eighth embodiment. FIG. 21 is a view showing a sequential luminance level during the freeze action according to the eighth embodiment.

In Step S801, the liquid crystal shutter 35 is driven and the impressed voltage of that is gradually increased such that the intensity of light that enters into the incidence surface 56A, namely, the light-amount for the subject S increases gradually. At this time the molecular arrangement changes so as to gradually increase the light-amount. Whereas, the motion of the diaphragm 33 is temporarily suspended to maintain the present opening-degree, and the electronic shutter action with the normal electronic shutter speed (=$\frac{1}{60}$ of a second) is performed for the CCD 54. In Steps S802 and S803, similarly to Steps S202 and S203 in FIG. 3, the luminance value Y is calculated, and it is determined whether the luminance value Y substantially coincides with the still-image standard luminance value Y2. When it is determined that the luminance value Y coincides with the still-image standard luminance value Y2, the process goes to Step S804. In Step S804, the liquid crystal shutter 35 is controlled in accordance with a control signal for the liquid crystal driver such that the molecular arrangement situation in the liquid crystal shutter 35 is maintained. A time TR is a time for making the molecular arrangement situation stable.

The performances of Steps S805 and S806 respectively correspond to the performances of Steps S205 and S206 in FIG. 3. Namely, the high-speed electronic shutter action is performed, the recording process is performed, and the still-image is displayed on the monitor 60.

In this way, in the eighth embodiment, when the freezing switch button 58 is turned ON, the liquid crystal shutter 35 is driven such that the luminance value Y coincides with the still-image standard luminance value Y2. Note that, a polarizing filter composed of a ceramic member may be applied as a transmitting member, in place of the liquid crystal shutter 35.

Figure 22:
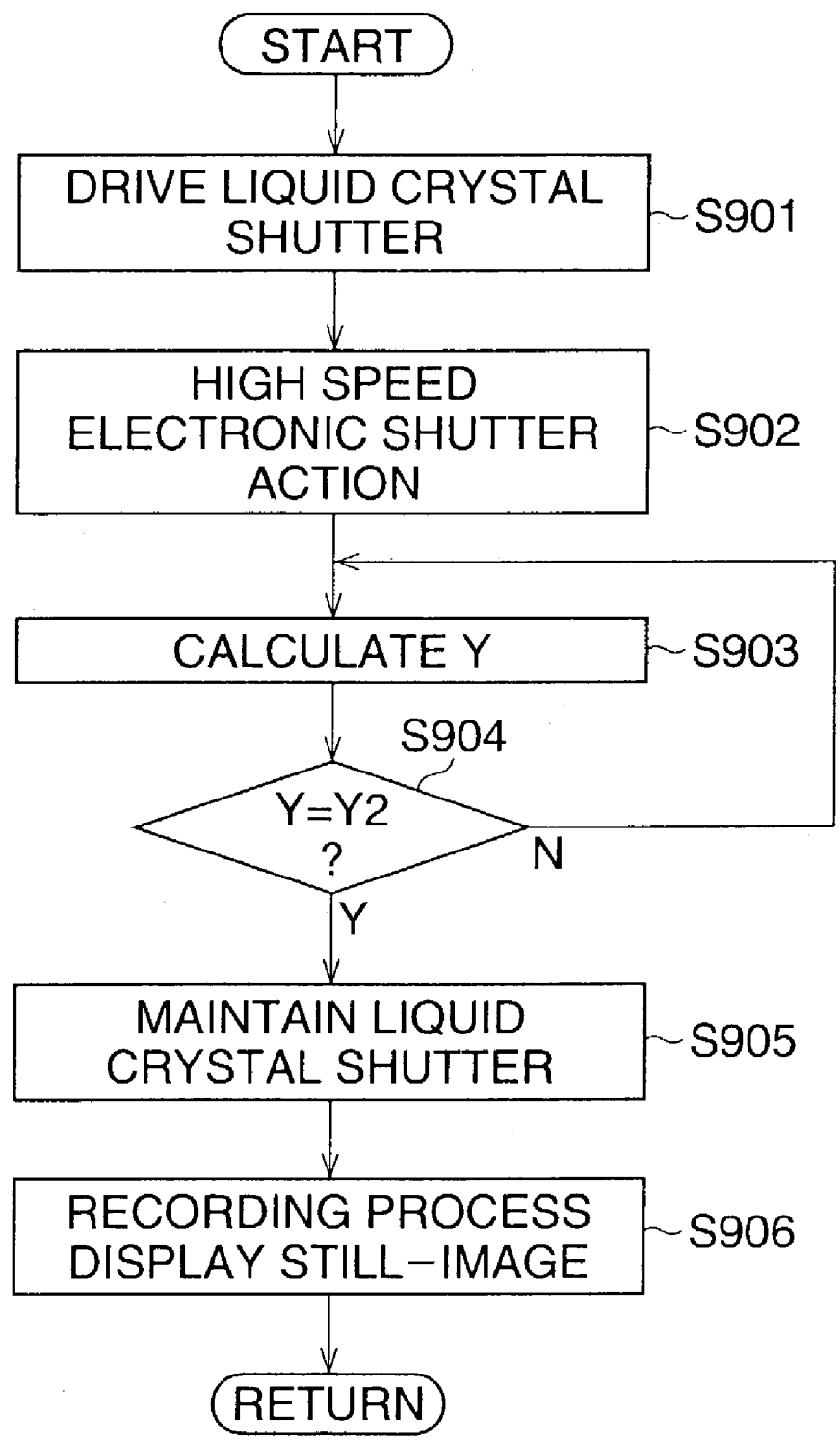
FIG. 22 is a view showing a process associated with the freeze action according to the ninth embodiment.
Figure 23:
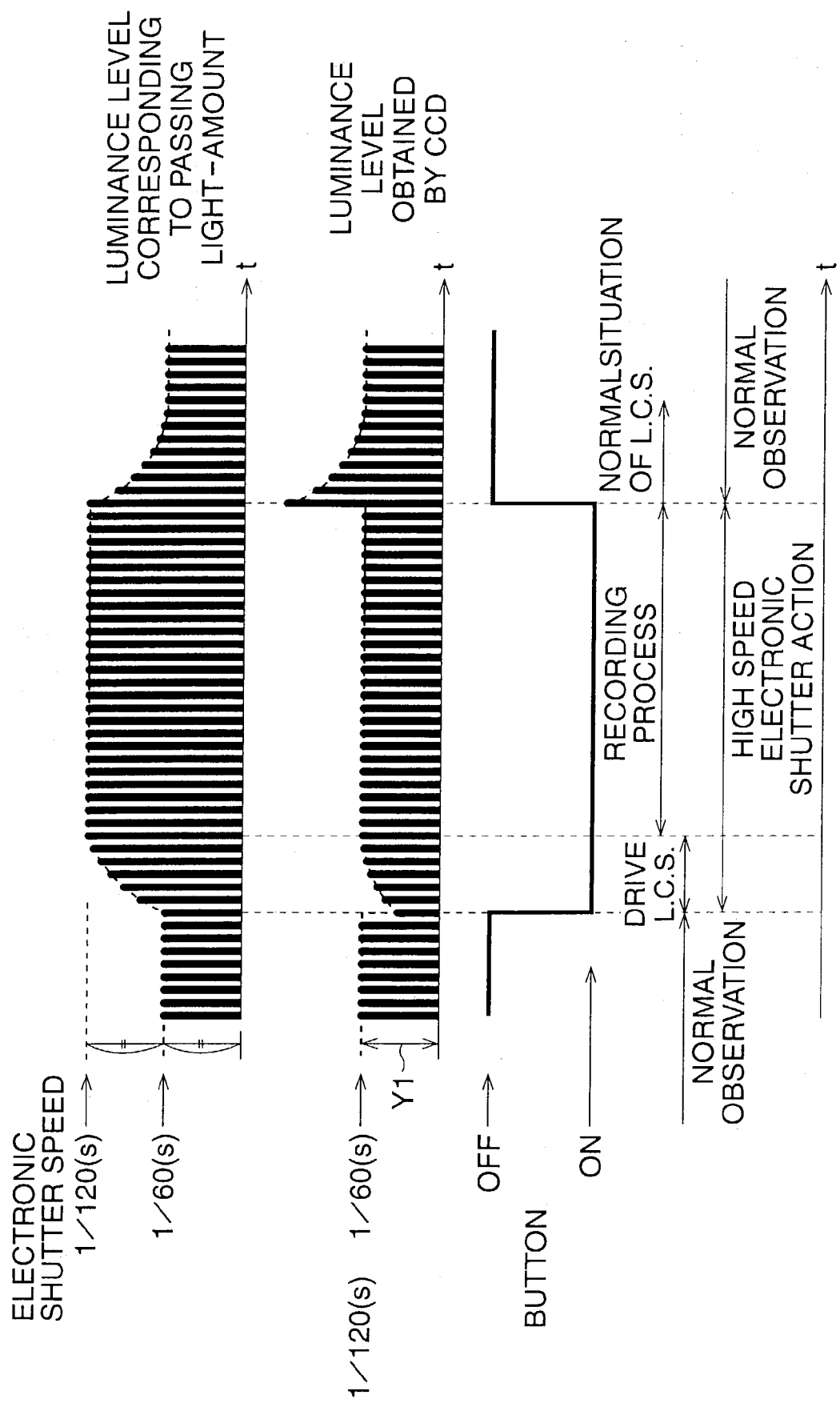
FIG. 23 is a view showing a sequential luminance level during the freeze action according to the ninth embodiment.

With reference to FIGS. 22 and 23, the ninth embodiment is explained. The ninth embodiment is different from the eighth embodiment in that the high-speed electronic shutter action is performed immediately after the freeze action is started, similarly to the second embodiment.

FIG. 22 is a view showing a process associated with the freeze action according to the ninth embodiment. FIG. 23 is a view showing a sequential luminance level during the freeze action according to the ninth embodiment.

In Step S901, similarly to Step S801 in FIG. 20, the liquid crystal shutter 35 is driven such that the light-amount for the subject S increases gradually. The performance of Steps S902 to S904 respectively corresponds to the performance of Steps S302 to S304 in FIG. 5 according to the second embodiment. Namely, the high-speed electronic shutter action is performed, and it is determined whether the luminance value Y substantially coincides with the still-image standard luminance value Y2. When the luminance value Y substantially coincides with the still-image standard luminance value Y2, the process goes to Step S905. In Step 905, similarly to Steps 804 in FIG. 20, the liquid crystal shutter 35 is controlled in accordance with a control signal for the liquid crystal driver such that the molecular arrangement situation in the liquid crystal shutter 35 is maintained. In Step S906, similarly to Steps S806 in FIG. 20, the high-speed electronic shutter action is performed, the recording process is performed, and the still-image is displayed on the monitor 60.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Applications No. 2002-114323 (filed on Apr. 17, 2002), No. 2002-114505 (filed on Apr. 17, 2002), No. 2002-114833 (filed on Apr. 17, 2002), and No. 2002-266688 (filed on Sep. 12, 2002), which are expressly incorporated herein, by reference, in their entireties.

The invention claimed is:

1. An electronic endoscope apparatus including a videoscope with an image sensor, comprising:
    a moving-image displayer that reads image-pixel signals from said image sensor at a predetermined time interval and processes the image-pixel signals, to display a moving-image;
    a light-amount adjuster that adjusts a light-amount, the light-amount being an amount of light for illuminating a subject; and
    a still-image recorder that performs a series of actions for recording a still image as data, said still-image recorder being configured to perform a high-speed electronic shutter action that enables the image-pixel signals to be read at a still-image electronic shutter speed, which corresponds to a reading time interval shorter than the predetermined time interval,
    wherein said still-image recorder controls the light-amount adjuster such that the light-amount increases until it becomes a standard light-amount corresponding to a recording of the still-image, when the series of actions is started, and
    wherein said still-image recorder performs a recording process that records the still-image as data in accordance with the still-image electronic shutter speed when the light-amount has become the standard light-amount.

2. The electronic endoscope apparatus of claim 1, wherein said still-image recorder comprises a light-amount determiner that determines whether the light-amount has become the standard light-amount,
    wherein said still-image recorder prohibits the recording process until it is determined that the light-amount has become the standard light-amount.

3. The electronic endoscope apparatus of claim 1, wherein said light-amount adjuster comprises a diaphragm that is provided in a light-path of the light emitted from a light source for illuminating the subject, said light-amount adjuster driving said diaphragm such that the light-amount becomes said standard light-amount.

4. The electronic endoscope apparatus of claim 2, wherein said still-image recorder controls said light-amount adjuster so as to gradually increase the light amount.

5. The electronic endoscope apparatus of claim 2, wherein said light-amount adjuster comprises a diaphragm that is provided in a light-path of the light emitted from a light source for illuminating the subject, said still-image recorder opening said diaphragm gradually until the light-amount becomes said standard light-amount.

6. The electronic endoscope apparatus of claim 1, wherein the standard light-amount is predetermined in accordance with a ratio of the reading time interval to the predetermined time interval, such that brightness of the still-image is substantially the same as that of the moving-image.

7. The electronic endoscope apparatus of claim 2, further comprising a luminance calculator that calculates a luminance value, indicating the brightness of a subject image, on the basis of the image-pixel signals,
    wherein said light-amount determiner determines whether the luminance value becomes a still-image standard luminance value corresponding to the standard light-amount.

8. The electronic endoscope apparatus of claim 1, further comprising an automatic light-amount adjusting processor that controls said light-amount adjuster on the basis of a moving-image standard light-amount, corresponding to standard brightness of the moving-image, to maintain proper brightness of the moving image.

9. The electronic endoscope apparatus of claim 1, wherein said still-image recorder prohibits performing the high-speed electronic shutter action and the recording process, until the light amount becomes the standard light-amount.

10. The electronic endoscope apparatus of claim 1, wherein said still-image recorder performs the high-speed electronic shutter action while prohibiting the recording process, until the light-amount becomes the standard light-amount.

11. The electronic endoscope apparatus of claim 1, further comprising a recording starting member for starting the series of actions.

12. The electronic endoscope apparatus of claim 1, further comprising a provisional still-image displayer that displays a provisional still-image when the series of actions is started, the provisional still-image displayer continually displaying the provisional still-image until the light-amount becomes the standard light-amount.

13. The electronic endoscope apparatus of claim 1, wherein said still-image recorder sets a control-amount necessary for achieving the standard light-amount, and controls said light-amount adjuster by the control-amount.

14. The electronic endoscope apparatus of claim 13, wherein said light-amount adjuster increases or decreases the light-amount in accordance with a light-amount adjusting parameter, and
    wherein said still-image recorder determines a change-amount of the light-amount adjusting parameter, which is necessary for achieving the standard light-amount, and controls the light-amount adjuster in accordance with the determined change-amount.

15. The electronic endoscope apparatus of claim 14, wherein said light-amount adjuster includes a pivotable diaphragm that has an insulating member provided in a light-path of the light emitted from a light source for illuminating the subject, the light-amount varying with an angle of said pivotable diaphragm,
    wherein said still-image recorder sets a change angle-amount for achieving the standard light-amount, and pivots said diaphragm by the change angle-amount.

16. The electronic endoscope apparatus of claim 13, wherein said light-amount adjuster comprises a liquid crystal shutter that is provided in a light-path of the light emitted from a light source for illuminating the subject, said liquid crystal shutter changing the light-amount in accordance with an applied voltage, wherein said still-image recorder sets a change voltage-amount for achieving the standard light-amount, and drives said liquid crystal shutter by the change voltage-amount.

17. The electronic endoscope apparatus of claim 14, wherein the light-amount changes by a constant change-amount as the light-amount adjusting parameter changes by the constant change-amount.

18. The electronic endoscope apparatus of claim 1, wherein said light-amount adjuster comprises:

a moving-image light-amount adjuster that adjusts the light-amount for the subject to adjust the brightness of the moving-image; and a still-image light-amount adjuster that changes the light-amount for the subject to the standard light-amount when performing the series of actions, wherein said still-image recorder controls said still-image light-amount adjuster such that the light-amount becomes the standard light-amount.

19. The electronic endoscope apparatus of claim 18, wherein said moving-image light-amount adjuster has a diaphragm provided in a light-path of the light emitted from a light source.

20. The electronic endoscope apparatus of claim 19, wherein said still-image light-amount adjuster is positioned between said light source and said diaphragm, and comprises a transmitting member configured to adjust a transmitting-amount of light from said light source.

21. The electronic endoscope apparatus of claim 20, wherein said transmitting member is a liquid crystal shutter.

22. The electronic endoscope apparatus of claim 18, wherein said still-image light-amount adjuster is positioned in a light-path of the light emitted from a light source, and comprises a transmitting member configured to adjust a transmitting-amount of the light from said light source.

23. An apparatus for recording a still-image from an electronic endoscope apparatus including a video-scope with an image sensor, comprising:

a high-speed electronic shutter processor that reads image-pixel signals from said image sensor at a still image electronic shutter speed, which corresponds to a reading time interval shorter than a predetermined time interval defined for displaying a moving-image;

a still-image light-amount controller that controls a light-amount adjuster for adjusting a light-amount, the light-amount being an amount of light for illuminating a subject, such that the light-amount increases until it becomes a standard light-amount corresponding to a recording of the still-image, when a series of actions for recording a still-image as data is started; and a recording processor that records the still-image as data in accordance with the still-image electronic shutter speed when the light-amount becomes the standard light-amount.

24. A computer readable medium comprising a computer program for recording a still-image from an electronic endoscope apparatus including a video-scope with an image sensor, the computer readable medium comprising:

an electronic shutter code segment that causes a high-speed electronic shutter processor to control said image at a still-image electronic shutter speed, which corresponds to a reading time interval shorter than a predetermined time interval defined for displaying a moving-image;

a light-amount control code segment that causes a still-image light-amount controller to control a light-amount adjuster for adjusting a light-amount, the light-amount being an amount of light for illuminating a subject, such that the light-amount increases until it becomes a standard light-amount corresponding to a recording of the still-image, when a series of actions for recording a still-image as data is started; and a recording code segment that causes a recording processor to record the still-image as data in accordance with the still-image electronic shutter speed when the light-amount becomes the standard light-amount.

25. A method for recording a still-image from an electronic endoscope apparatus including a video-scope with an image sensor, the method comprising:

reading image-pixel signals from said image sensor at a still-image electronic shutter speed, which corresponds to a reading time interval shorter than a predetermined time interval defined for displaying a moving-image;

controlling a light-amount adjuster for adjusting a light-amount, the light-amount being an amount of light for illuminating a subject, such that the light-amount increases until it becomes a standard light-amount corresponding to a recording of the still image, when a series of actions for recording a still-image as data is started, and recording the still-image as data in accordance with the still-image electronic shutter speed when the light-amount becomes the standard light amount.

* * * * *